(12) United States Patent
Sandell et al.

(10) Patent No.: US 7,964,360 B2
(45) Date of Patent: Jun. 21, 2011

(54) UNCOUPLED COLLAGEN SYNTHESIS AND DEGRADATION ASSAYS

(75) Inventors: Linda J. Sandell, St. Louis, MO (US); Patrick Garnero, Gaujac (FR)

(73) Assignee: Barnes-Jewish Hospital, St. Louis, MO (US)

( * ) Notice: Subject to any disclaimer, the term of this patent is extended or adjusted under 35 U.S.C. 154(b) by 415 days.

(21) Appl. No.: 11/758,471

(22) Filed: Jun. 5, 2007

(65) Prior Publication Data

US 2007/0292892 A1 Dec. 20, 2007

Related U.S. Application Data

(63) Continuation of application No. 10/705,124, filed on Nov. 10, 2003, now abandoned.

(60) Provisional application No. 60/424,941, filed on Nov. 8, 2002.

(51) Int. Cl.
*G01N 33/53* (2006.01)

(52) U.S. Cl. ........ 435/7.1; 435/1.1; 435/7.21; 435/7.92; 435/7.94; 435/979; 436/509; 436/811

(58) Field of Classification Search ............. 435/1.1, 435/6, 7.1, 7.21, 7.92–7.94, 973; 436/501, 436/509, 518, 524, 528, 15, 811
See application file for complete search history.

(56) References Cited

U.S. PATENT DOCUMENTS

| | | | |
|---|---|---|---|
| RE35,306 E | 7/1996 | Chen | |
| 5,541,066 A | 7/1996 | Sandell | |
| 5,602,040 A | 2/1997 | May | |
| 5,780,240 A | 7/1998 | Sandell | |
| 5,782,240 A | 7/1998 | Raviv | |
| 5,935,796 A | 8/1999 | Fosang | |
| 6,132,976 A | 10/2000 | Poole et al. | |
| 6,352,862 B1 | 3/2002 | Davis | |
| 6,642,007 B1 | 11/2003 | Saltarelli et al. | |

OTHER PUBLICATIONS

Sharif et al., A 5-year longitudinal study of Type IIa Collagen Synthesis and total Type II collagen degradation in patient with knee osteoarthritis—association with disease progression, Rheumatology 46 (6): 938-943 (Mar. 26, 2007).*

Garnero et al., Uncoupling of Type II Collagen Synthesis and Degradation Predicts Progression of Joint Damage in Patients with Knee Osteoarthritis, Arthritis and Rheumatism 46(10): pp. 2613-2624 (Oct. 2002).*

Aigner T, et al., Re-expression of type II A procollagen by adult articular chondrocytes in osteoarthritic cartilage, Arthritis Rheum., 1999, p. 1443-50, vol. 42(7).

(Continued)

*Primary Examiner* — Gailene R Gabel
(74) *Attorney, Agent, or Firm* — SNR Denton US LLP

(57) ABSTRACT

The invention relates to methods for determining the progression of cartilage degeneration diseases, such as osteoarthritis and rheumatoid arthritis, by quantitating collagen synthesis and degradation markers in patient samples. One can determine whether a cartilage degeneration condition is progressing, regressing, or remaining stable by quantitating collagen synthesis and degradation markers in patient samples and comparing the value obtained to a reference value. When a joint affected by cartilage degeneration in question expresses collagen synthesis and degradation markers, a change in this value is indicative of a change in the progression of the cartilage degeneration condition. The methods and apparatus of the invention allow accurate determination of the therapeutic effects certain cartilage degeneration drug treatments, including osteoarthritis and rheumatoid arthritis drug treatments, so are also useful for pharmaceutical efficacy studies in mammals.

13 Claims, 5 Drawing Sheets

OTHER PUBLICATIONS

Ayral X, et al., Chondroscopy: a new method for scoring chondropathy, Semin. Arthritis Rheum., 1993, p. 289-97, vol. 22(5).

Ayral X, et al., Arthroscopic evaluation of chondropathy in osteoarthritis of the knee, J. Rheumatol., 1996, p. 698-706, vol. 23(4).

Billinghurst RC, et al., Enhanced cleavage of type II collagen by collagenase in osteoarthritic articular cartilage, J. Clin. Invest., 1997, p. 1534-1545, vol. 99.

Campbell CJ, The healing of cartilage defects, Clin. Orthop. Relat. Res., 1969, p. 45-63, vol. 64.

Christgau S, et al., Collagen type II C-telopeptide fragments as an index of cartilage degradation, Bone, 2001, p. 209-15, vol. 29(3).

Conrozier T, et al., Serum concentrations of cartilage oligomeric matrix protein and bone sialoprotein in hip osteoarthritis: A one year prospective study, Ann. Rheum. Dis., 1998, p. 527-32, vol. 57(9).

Dean DD, et al., Evidence for metalloproteinase and metalloproteinase inhibitor imbalance in human osteoarthritic cartilage, J. Clin. Invest., 1989, p. 678-85, vol. 84(2).

Downs JT, et al., Analysis of collagenase-cleavage of type II collagen using a neoepitope ELISA, J. Immunol. Methods, 2001, p. 25-34, vol. 247(1-2).

Eastell R, et al., Evaluation of bone turnover in type I osteoporosis using biochemical markers specific for both bone formation and bone resorption, Osteoporos Int., 1993, p. 255-60, vol. 3(5).

Fife RS, et al., Relationship between arthroscopic evidence of cartilage damage and radiographic evidence of joint space narrowing in early osteoarthritis of the knee, Arthritis Rheum., 1991, p. 377-82, vol. 34(4).

Garnero P, et al., Molecular basis and clinical use of biochemical markers of bone, cartilage and synovium in joint diseases, Arthritis Rheum., 2000, p. 953-61, vol. 43(5).

Garnero P, et al., Cross sectional evaluation of biochemical markers of bone, cartilage, and synovial tissue metabolism in patients with knee osteoarthritis: relations with disease activity and joint damage, Ann. Rheum. Dis., 2001, p. 619-26, vol. 60(6).

Georges C, et al., Serum biologic markers as predictors of disease progression in osteoarthritis of the knee, Arthritis Rheum., 1997, p. 590-1, vol. 40(3).

Hollander AP, et al., Increased damage of type II collagen in osteoarthritic articular cartilage detected by a new immunoassay, J. Clin. Invest., 1994, p. 1722-32, vol. 93(4).

Hollander A.P., et al., Damage to type II collagen in aging and osteoarthritis starts at the articular surface, originates around chondrocytes and extends into the cartilage with progressive degeneration, J. Clin. Invest, 1995, p. 2859-69, vol. 96(6).

Kim HK, et al., The potential for regeneration of articular cartilage in defects created by chondral shaving and subchondral abrasion: an experimental investigation in rabbits, J. Bone Joint Surgery Am., 1991, p. 1301-15, vol. 73(9).

Lui VC, et al., Tissue-specific and differential expression of alternatively spliced alpha 1 (II) collagen mRNAs in early embryos, Dev. Dyn., 1995, p. 198-211, vol. 203(2).

Moskowitz RW, et al., Abstract, Type II C-telopeptide 2B4 epitope is a marker for cartilage degradation in familial osteoarthritis, Arthritis Rheum., 1998, p. S352, vol. 41 (Suppl).

Nah HD, Type II collagen mRNA containing an alternatively spliced exon predominates in the chick limb prior to chondrogenesis, J. Biol. Chem., 1991, p. 23446-52, vol. 266(34).

Nah HD, et al., Type IIA procollagen: Expression in developing chicken limb cartilage and human osteoarthritic articular cartilage, Dev. Dyn., 2001, p. 307-22, vol. 220(4).

Nelson F, et al., Evidence of altered synthesis of type II collagen in patients with osteoarthritis, J. Clin. Invest., 1998, p. 2115-25, vol. 102(12).

Oganesian A, et al., Type IIA procollagen amino propeptide is localized in human embryonic tissues, J. Histochem. Cytochem., 1997, p. 1469-80, vol. 45(11).

Otterness IG, et al. An analysis of 14 molecular markers for monitoring osteoarthritis: segregation of the markers into clusters and distinguishing osteoarthritis at baseline, Osteoarthritis and Cartilage, 2000, p. 180-5, vol. 8(3).

Poole AR, Cartilage in health and disease. In: Koopman W.J., ed., Arthritis and Allied Conditions: A Textbook of Rheumatology, 1997, Baltimore: Williams & Wilkins, 13 ed., pp. 255-308.

Ravaud P, et al., Variability in knee radiographing: implication for definition of radiological progression in medial knee osteoarthritis, Ann. Rheum. Dis., 1998, p. 624-9, vol. 57(10).

Rousseau JC, et al., Abstract, Serum levels of type II A procollagen amino terminal propeptide (PIIANP) are decreased in patients with knee osteoarthritis and rheumatoid arthritis, Arthritis Rheum., 2000, p. S351, vol. 43 (Suppl).

Ryan MC and Sandell LJ, Differential expression of a cysteine-rich domain in the amino-terminal propeptide of type II (cartilage) procollagen by alternative splicing of mRNA, J. Biol. Chem., 1990, p. 10334-9, vol. 265(18).

Sandell LJ, et al., Alternatively spliced type II procollagen mRNAs define distinct populations of cells during vertebral development: differential expression of the amino-propeptide, J. Cell. Biol., 1991, p. 1307-19, vol. 114(6).

Sandell LJ, et al., Alternative splice form of type II procollagen mRNA (IIA) is predominant in skeletal precursors and non-cartilaginous tissues during early mouse development, Dev. Dyn., 1994, p. 129-140, vol. 199(2).

Sharif M, et al., Serum hyaluronic acid level as a predictor of disease progression in osteoarthritis of the knee, Arthritis Rheum., 1995, p. 760-7, vol. 38(6).

Sharif M, et al., Relationship between serum cartilage oligomeric matrix protein levels and disease progression in osteoarthritis of the knee joint, Brit. J. Rheumatol., 1995, p. 306-10, vol. 34(4).

Spector TD, et al., Low-levels increases in serum C-reactive protein are present in early osteoarthritis of the knee and predict progressive disease, Arthritis Rheum., 1997, p. 723-7, vol. 40(4).

Antibodies, A Laboratory Manual, Harlow and Lane, eds., Cold Spring Harbor Laboratory, Ch. 9, (1988).

Altman et al., Development of criteria for the classification and reporting of osteoarthritis. Classification of osteoarthritis of the knee. Arthritis Rheum, 1986, p. 1039-1049, vol. 29.

Ayral et al., Progression of the knee osteoarthritis assessed by arthroscopy: a multicenter, randomized, double blind comparison of tenidap sodium versus piroxicam [Abstract], Ann Rheum Dis, 2000, p. S54, vol. 59.

Avrameas et al., Coupling of enzymes to antibodies and antigens, Scan J Immunol, 1978, p. 7, vol. 8.

Bayer et al., The avidin-biotin complex in affinity cytochemistry, Meth Enzymol, 1979, p. 308-315, vol. 62.

Bland et al., Statistical methods for assessing agreement between two methods of clinical measurement, Lancet, 1986, p. 307-310, vol. i.

Boudreault et al., Molecular characterization, enzymatic analysis and purification of murine proprotein convertase-1/3 (PC1/PC3) secreted from recombinant baculovirus-infected insect cells, Protein Expression and Purification, 1998, p. 353-366, vol. 14.

Chandler et al., An investigation of the use of urease-antibody conjugates in enzyme immunoassay, J Immunol Meth, 1982, p. 187-194, vol. 53.

Cole et al., Monoclonal antibodies and cancer therapy, Alan R. Liss, ed., 1985, p. 77-96.

Cote et al., Generation of human monoclonal antibodies with reactive cellular antigens, PNAS, 1983, p. 2026-2030, vol. 80.

Dudley, The ciba corning ACS:180 automated immunoassay system, J Clin Immunoassay, 1991, p. 77, vol. 14.

Ekeke et al., Immunofluorimetric assay of oestradiol-17(beta), J Steroid Biochem, 1979, p. 1597-1600, vol. 11.

Felson, Epidemiology of osteoarthritis, Osteoarthritis, Oxford University Press, 1998, p. 13-22.

Garnero et al., Increased bone turnover in late postmenopausal women is a major determinant of osteoporosis, J Bone Miner Res, 1996, p. 337-349, vol. 11.

Garnero et al., Uncoupling of type II collagen synthesis and degradation predicts progression of joint damage in patients with osteoarthritis, Arthritis Rheum, 2002, p. 2613-2624, vol. 46.

Geoghegan et al., The detection of human B lymphocytes by both light and electron microscopy utilizing collodial gold labeled anti-immunoglobulin, Immunol Comm, 1978, p. 1-12, vol. 7.

Goldberg et al., Elevated plasma levels of hyaluronate in patients with osteoarthritis and rheumatoid arthritis, Athritis Rheum, 1991, p. 799-807, vol. 34.

Kobayashi et al., Synovial fluid concentrations of the C-propeptide of type II collagen correlate with body mass index in primary knee osteoarthritis, Ann Rheum Dis, 1997, p. 500-503, vol. 56.

Kohler et al., Continuous cultures of fused cells secreting antibody of predefined specificity, Nature, 1975, p. 495-497, vol. 256.

Kricka, Chemiluminescence and Bioluminescence, Analysis by, Molecular Biology and Biotechnology: A Comprehensive Desk Reference, RA Meyers, ed., VCH Publishers, NY, NY, 1995, p. 165-167.

Lane et al., Reliability of new indices of radiographic osteoarthritis of the hand and hip and lumbar spine degeneration, J Rheumatol, 1993, p. 1911-1918, vol. 20.

Lequeasne et al., Indexes of severity for osteoarthritis of the hip and knee. Validation-value in comparison with other assessment tests, Scand J Rheumatol, 1987, p. 85-89, suppl. vol. 65.

Lohmander et al., Procollagen II C-propeptide in joint fluid: changes in concentration with age, time after knee injury and osteoarthritis, J Rheumatol, 1996, p. 1765-1769, vol. 23.

Morrison et al., Chimeric human antibody molecules: mouse antigen-binding domains with human constant region domains, PNAS, 1984, p. 6851-6855, vol. 81.

Neuberger et al, Recombinant antibodies possessing novel effector functions, Nature, 1984, p. 604-608, vol. 312.

Paralkar et al., Cloning and characterization of a novel member of the transforming growth factor (beta) / bone morphogenetic protein family, J Biol Chem, 1998, p. 13760-13767, vol. 273.

Principles and Practices of Immunoassay, Price and Newman, eds., McMillan, 1977, first three pages of book provided.

SAS Institute Inc. SAS STAT User's Guide, Version 6, 4th Edition, SAS Institute Inc., vol. 1 and 2, (1988).

Shinmei et al., Joint fluid carboxy-terminal type II procollagen peptide as a marker of cartilage biosynthesis, Osteoarthritis Cartilage, 1993, p. 121-128, vol. 1.

Shinmei et al., A significance of the level of carboxyterminal type II procollagen peptide, chondroitine sulfate isomers, tissue inhibitor of metalloproteinases and metalloproteinases in osteoarthritis joint fluid, J Rheumatol, 1995, p. 78-81, vol. 22 (suppl 43).

Szulc et al., Cross-sectional assessment of age-related bone loss in men: the MINOS study, Bone, 2000, p. 123-129, vol. 26.

Takeda et al., Construction of chimaeric processed immunoglobulin genes containing mouse variable and human constant region sequences, Nature, 1985, p. 452-454, vol. 314.

Wilson et al., Recent developments in the periodate method of conjugating horseradish peroxidase (HRPO) to antibodies, in Immunofluorescence and Related Staining Techniques, Elsevier Holland, 1978, p. 215-224.

International Search Report issued in connection with related Application No. PCT/US03/35637, (2003).

Canadian Office Action issued in connection with related Canadian Application No. 2,502,926, (2001).

* cited by examiner

UNCOUPLED COLLAGEN SYNTHESIS AND DEGRADATION ASSAYS

CROSS-REFERENCE TO RELATED APPLICATIONS

This application is a Continuation Application of U.S. application Ser. No. 10/705,124, filed Nov. 10, 2003, now abandoned, which claims priority to U.S. Prov. App. Ser. No. 60/424,941, filed Nov. 8, 2002, now expired, each of which are incorporated herein by reference in their entirety.

STATEMENT REGARDING FEDERALLY SPONSORED RESEARCH OR DEVELOPMENT

Not Applicable.

BACKGROUND OF THE INVENTION

The present invention relates in general to the field of medical diagnostics, and more particularly to assays for determining cartilage degeneration status, including cartilage degeneration status in osteoarthritis ("OA"), rheumatoid arthritis ("RA") status, and status in other arthritic conditions.

The hallmark of OA, the most common cartilage degeneration joint disease, and RA is cartilage loss leading to joint destruction. Knee OA, one of the most common forms of OA, is associated with significant morbidity (Felson, D. T., Epidemiology of Osteoarthritis. In: Brandt K. F., et al., eds., OSTEOARTHRITIS. Oxford University Press, pp. 13-22 (1998)).

To assess the progression of cartilage destruction the most established methods are the measurement of joint space width (JSW) using plain X-rays and the assessment of chondropathy by arthroscopic evaluation of the knee. These two techniques have however some limitations. When there is radiological evidence of OA, there is often already significant joint damage. Because changes of JSW are relatively small compared to the precision error of X-ray measurements, at least one year and preferably 2 years are usually necessary to accurately assess the progression of joint damage or its reduction by treatment (Ravaud, P., et al., Variability in knee radiographing: implication for definition of radiological progression in medial knee osteoarthritis, Ann. Rheum. Dis. 57:624-629 (1998)). Magnetic resonance imaging is more sensitive than plain X-ray, although its reproducibility is not yet fully validated and is currently being optimized for monitoring patients with OA.

Arthroscopy provides a direct and magnified view of the cartilage surface that has prompted some to consider arthroscopy as the gold standard for the assessment of cartilage lesions (Fife, R. S., et al., Relationships between arthroscopic evidence of cartilage damage and radiographic evidence of joint space narrowing in early osteoarthritis of the knee, Arthritis Rheum. 34:377-382 (1991); Ayral, X., et al., Chondroscopy: a new method for scoring chondropathy, Semin. Arthritis Rheum. 22:289-297 (1993)). Arthroscopic scoring systems of chondropathy have been established and validated (Aryal, X., Semin. Arthritis Rheum. 22, supra; Ayral, X., et al., Arthroscopic evaluation of chondropathy in osteoarthritis of the knee, J. Rheumatol. 23:698-706 (1996)). This is however an invasive technique which can not be routinely applied to all patients and which requires trained investigators. Clearly, for identifying patients at high risk for destructive OA and for monitoring drug efficacy there is a need for non-invasive methods that can be repeated and have improved sensitivity compared to plain X-rays.

Molecular markers are molecules or fragments thereof of tissue matrices which are released into biological fluids during the process of tissue biosynthesis and turnover and which can be measured by immunoassays. Molecular markers of bone, cartilage and synovium have been described and their changes have been investigated in patients with OA, mainly in cross-sectional studies (Garnero, P., et al., Molecular basis and clinical use of biochemical markers of bone, cartilage and synovium in joint diseases, Arthritis Rheum. 43:953-961 (2000)). However, detection of molecular markers for collagen synthesis or degradation has not been used to provide information on the progression of OA and other forms of cartilage degeneration.

Because the loss of cartilage is believed to result from the combination of a decreased reparative process coupled with an increased degradative phenomenon (Dean, D. D., et al., Evidence for metalloproteinase and metalloproteinase inhibitor imbalance in human osteoarthritic cartilage, J. Clin. Invest. 84:678-685 (1989); Poole, A. R., Cartilage in health and disease. In: Koopman W. J., ed., ARTHRITIS AND ALLIED CONDITIONS: A TEXTBOOK OF RHEUMATOLOGY, Baltimore: Williams & Wilkins, 13 ed., pp. 255-308 (1997)), thereby limiting the capacity of cartilage repair (Campbell, C. J., The healing of cartilage defects, Clin. Orthop. 64:45-63 (1969); Kim, H. K., et al., The potential for regeneration of articular cartilage in defects created by chondral shaving and subchondral abrasion: an experimental investigation in rabbits, J. Bone Joint Surgery Am. 73:1304-1315 (1991)) and because type II collagen is the most abundant protein of cartilage matrix, the assessment of type II collagen synthesis and degradation is an attractive approach for the investigation of OA and other cartilage degeneration conditions.

In vitro studies performed on cartilage tissue from patients with OA and controls have provided evidence of altered synthesis (Nelson, F., et al., Evidence of altered synthesis of type II collagen in patients with osteoarthritis, J. Clin. Invest. 102:2115-2125 (1998)). Certain immunoassays have indicated increased degradation of type II collagen in OA (Hollander, A. P., et al., Increased damage of type II collagen in osteoarthritic articular cartilage detected by a new immunoassay, J. Clin. Invest. 93:1722-1732 (1994); Billinghurst, R. C., et al., Enhanced cleavage of type II collagen by collagenase in osteoarthritic articular cartilage, J. Clin. Invest. 99:1534-1545 (1997); Hollander, A. P., et al., Damage to type II collagen in aging and osteoarthritis starts at the articular surface, originates around chondrocytes and extends into the cartilage with progressive degeneration, J. Clin. Invest. 96:2859-2869 (1995)). However, molecular markers that indicate both collagen synthesis and degradation have remained unavailable. Therefore, accurate and precise assessment of the level and/or progression of OA and other cartilage degenerative conditions in vitro and/or in vivo has remained a significant problem.

Type II collagen is synthesized as a procollagen molecule including the N-(PIINP) and C-(PIICP) propeptides at each end. Type II procollagen is produced in two forms as the result of alternative RNA splicing (Ryan, M. S., et al., Differential expression of a cystein-rich domain in the amino-terminal propeptide of type II (cartilage) procollagen by alternative splicing of messenger RNA, J. Biol. Chem. 265:10336-10339 (1990); Nah, H. D., et al., Type II collagen mRNA containing an alternatively spliced exon predominates in the chick limb prior to chondrogenesis, J. Biol. Chem. 266:23446-23452 (1991)). One form (IIA) includes and the other form (IIB) excludes a 69 amino acid cysteine-rich globular domain encoded by exon 2 in the PIINP. Type IIB procollagen is expressed at high levels in well-differentiated chondrocytes, forming the framework of normal adult cartilage. On the other hand, type IIA procollagen is temporally expressed in pre-chondrogenic condensing limb mesenchyme, sclerotome and early cartilage (Sandell, L. J., et al., *Alternatively spliced type II procollagen mRNAs define distinct populations of cells during vertebral development: differential expression of the amino-propeptide*, J. Cell. Biol. 114:1307-1319 (1991); Sandell, L. J., et al., *Alternative splice form of type II procollagen mRNA (IIA) is predominant in skeletal precursors and non-cartilaginous tissues during early mouse development*, Dev. Dyn. 199:129-140 (1994); Lui, V. C., et al., *Tissue-specific and differential expression of alternatively spliced alpha 1 (II) collagen mRNAs in early embryos*, Dev. Dyn. 203:198-211 (1995); Oganesian, A., et al., *Type IIA procollagen amino propeptide is localized in human embryonic tissues*, J. Histochem. Cytochem. 45:1469-1480 (1997)) and can be re-expressed later in the development at the onset of cartilage hyperthrophy (Nah, H. D., et al., *Type IIA procollagen: Expression in developing chicken limb cartilage and human osteoarthritic articular cartilage*, Dev. Dyn. 220:307-322 (2001)). In addition it has recently been shown that type IIA procollagen is re-expressed by adult articular chondrocytes of affected human osteoarthritic cartilage (Nah, Dev. Dyn. 220, supra; Aigner, T., et al., *Re-expression of type IIA procollagen by adult articular chondrocytes in osteoarthritic cartilage*, Arthritis Rheum. 42:1443-1450 (1999)). During secretion and before incorporation of type II collagen molecules into cartilage matrix, the N and C propeptides are removed by specific enzymes and released in part into the synovial fluid and cleared into the blood. The serum level of these propeptides is thus believed to represent an adequate index of the rate of type II collagen synthesis. The first assays developed to investigate type II collagen synthesis were for PIICP. Nelson, et al. (J. Clin. Invest. 102, supra) showed that PIICP is a valid index of the rate of type II collagen synthesis in healthy and OA cartilage and that serum PIICP levels were decreased in patients with OA. An ELISA was developed for measuring specifically the N-propeptide of type IIA procollagen (PI-IANP) with no significant cross-reactivity with type I collagen N-propeptide and reported decreased serum levels of PIIANP in patients with knee OA and RA compared to age-matched healthy controls suggesting a deficit of type II collagen synthesis in joint diseases (Rousseau, J-C., et al., Abstract, *Serum levels of type II A procollagen amino terminal propeptide (PIIANP) are decreased in patients with knee osteoarthritis and rheumatoid arthritis*, Arthritis Rheum. 43 (supp.):S351 (2000)).

To assess type II collagen degradation, immunoassays using antibodies recognizing either neo-epitopes generated by denaturation of the triple helix domain of type II collagen (Hollander, J. Clin. Invest. 93, supra; Downs, J. T., et al., *Analyis of collagenase-cleavage of type II collagen using a neoepitope ELISA*, J. Immunol. Methods 247:25-34 (2001)) or cross-linked fragments of the telopeptides (Moskowitz, R. W., et al., Abstract, *Type II C-telopeptide 2B4 epitope is a marker for cartilage degradation in familial osteoarthitis*, Arthritis Rheum. 41 (supp.):S352 (1998); Christgau, S., et al., *Collagen type II C-telopeptide fragments as an index of cartilage degradation*, Bone 29:209-215 (2001)) have been recently developed. Using an assay recognizing C-terminal cross-linking telopeptide of type II collagen (CTX-II) in urine (Christgau, supra), subjects of a cross sectional study showed increased levels of urinary CTX-II in patients with knee OA (Garnero, P., et al., *Cross sectional evaluation of biochemical markers of bone, cartilage, and synovial tissue metabolism in patients with knee osteoarthritis: relations with disease activity and joint damage*, Ann. Rheum. Dis. 60:619-626 (2001)).

Some methods of detecting OA are presently known in the art. For example, U.S. Pat. No. 5,780,240 to Sandell, incorporated herein by reference in its entirety, describes assays to detect cartilage synthesis in OA patients. The assays are useful in providing methods for detecting type IIA mRNA and/or type IIA procollagen/propeptide in samples from non-embryonic individuals. However, while the methods allow determination of whether a patient has OA, they do not provide a method for determining the progress of OA in a patient, how to determine the rate of progression of the disease, how to determine the likelihood of increased or decreased OA progress, nor how to determine the efficacy of drugs on the progress of OA. Likewise, U.S. Pat. No. 5,541,066 to Sandell, incorporated herein by reference in its entirety, describes assays for determining cartilage synthesis associated with osteoarthritis, but also fails to overcome the limitations in the art with respect to evaluating the progress of disease in a patient with OA.

A cross-sectional study of multiple (fourteen) molecular markers for monitoring osteoarthritis has been described. The markers of inflammation, bone, cartilage and synovium metabolism were segregated into clusters and used in distinguishing osteoarthritis at baseline. Otterness et al., *An analysis of 14 molecular markers for monitoring osteoarthritis: segregation of the markers into clusters and distinguishing osteoarthritis at baseline*, Osteoarthritis and Cartilage 8:180-185 (2000). Using a principal component analysis, as opposed to an uncoupling analysis, the study reported that molecular markers reflecting cartilage synthesis (serum aggregan epitope 846 and PIICP) and those of cartilage catabolism (serum cartilage oligomeric matrix protein (COMP) and keratan sulfate) segregated into two separate and independent factors and that the combination of these two groups together with tumor necrosis factor receptor type II (a marker of inflammation) provided the best discrimination between patient with knee OA and healthy controls. However, only three markers (tumor necrosis factor receptor II, cartilage oligomeric matrix protein and epitope 846) from independent clusters minimally discriminated osteoarthritis patients from controls. A conclusion of the study was that better markers are needed to accurately and precisely determine the status of osteoarthritis in subjects.

The use of molecular markers of bone formation and bone resorption to determine type I osteoporosis has been described. Eastell, R. et al, *Evaluation of bone turnover in type I osteoporosis using biochemical markers specific for both bone formation and bone resorption*, Osteoporos Int. 3:255-260 (1993). However, bone synthesis and degradation markers are not associated with collagen synthesis and degradation markers and are not predictive whether such collagen markers could be used in a predictive way with osteoarthritis, rheumatoid arthritis and other cartilage degeneration conditions.

Accordingly, there is a need for cartilage markers that can provide information on collagen metabolism and the progression of the arthritic disease state. Such markers would be useful in estimating the progression of cartilage degeneration diseases such as OA and RA. In addition, such markers would allow accurate determination of the therapeutic effects certain cartilage degeneration drug treatments, including osteoarthritis and rheumatoid arthritis drug treatments, so would be useful for pharmaceutical efficacy studies in mammals.

BRIEF SUMMARY OF THE INVENTION

The present invention is based in part on the surprising discovery that decreased serum PIIANP levels, when associated with high cartilage degradative markers, are associated with a fast rate of cartilage loss and alterations of type II collagen synthesis in the signal joint. No correlation between serum PIIANP and urinary CTX-II in patients with knee OA exists, suggesting that the rate of synthesis of type II collagen molecules is independent of the rate of degradation of resident molecules within cartilage matrix in favor of an uncoupling of these two activities. In addition, the invention is based in part on the surprising discovery that the combination of a marker of cartilage synthesis (PIIANP) with that of catabolism (CTX-II) in an uncoupling index improves the ability to discriminate between patients with knee OA and controls as compared with using one of these two markers alone.

Accordingly, in an exemplary embodiment there is provided a method for detecting or predicting cartilage destruction in a subject, the method comprising detecting an uncoupling of type II collagen synthesis from type II collagen degradation in the subject.

In another embodiment, there is provided a method for determining the progress of osteoarthritis or cartilage destruction in a subject comprising quantifying an uncoupling of type II collagen synthesis from type II collagen degradation in the subject In another embodiment, there is provided a method for detecting or predicting osteoarthritis in a subject, the method comprising the steps of (a) providing a first and a second body fluid sample, wherein the first sample is taken from a subject from which status of osteoarthritis is to be determined and the second sample is taken from the same subject at a later time, (b) providing a first antibody, second antibody, third labeled antibody, and fourth labeled antibody, wherein the first antibody is capable of specifically binding to a human collagen synthesis marker, the second antibody is capable of specifically binding to a human collagen degradation marker, the third labeled antibody is capable of binding to the human collagen synthesis marker, and the fourth labeled antibody is capable of binding to the human collagen degradation marker, and a detecting reagent capable of detecting the label, (c) contacting the first antibody, second antibody, third labeled antibody, fourth labeled antibody, and the detecting reagent with the first body fluid sample, (d) contacting the first antibody, second antibody, third labeled antibody, fourth labeled antibody, and the detecting reagent with the second body fluid sample, and (e) detecting the amount of and determining the concentration of human collagen synthesis marker and collagen degradation marker in the first sample to provide a reference value and detecting the amount of and determining the concentration of human collagen synthesis marker and collagen degradation marker in the second sample, wherein an increased concentration of human collagen degradation marker coupled with a decreased concentration of collagen synthesis marker in the second sample compared to the reference value indicates that the test subject has a high probability of having had or being at risk of progressive osteoarthritis.

In another embodiment, there is provided a method for detecting or predicting osteoarthritis in a subject, the method comprising the steps of (a) providing a body fluid sample, wherein the sample is taken from a subject from which status of osteoarthritis is to be determined, (b) providing a first antibody, second antibody and a third labeled antibody, wherein the first antibody is capable of specifically binding to a human collagen synthesis marker, the second antibody is capable of specifically binding to a human collagen degradation marker, and the third labeled antibody is capable of binding to both the human collagen synthesis marker and human collagen degradation marker, and a detecting reagent capable of detecting the label, (c) contacting the first antibody, second antibody, and the third labeled antibody, and the detecting reagent with the body fluid sample, (d) contacting the first antibody, second antibody and the third labeled antibody, and the detecting reagent with the body fluid sample, and (e) detecting the amount of and determining the concentration of human collagen synthesis marker and collagen degradation marker in the sample, wherein a concentration of human collagen degradation marker greater than one standard deviation above a predetermined reference value uncoupled with a decreased concentration of collagen synthesis marker less than one standard deviation below a predetermined reference value indicates that the test subject has a high probability of having had or being at risk of progressive osteoarthritis.

In another embodiment, there is provided a solid support in contact with a combination of a first antibody and second antibody, wherein the first antibody is capable of specifically binding to a human collagen synthesis marker and the second antibody is capable of specifically binding to a human collagen degradation marker.

In another embodiment, there is provided a kit for detecting the progression of osteoarthritis comprising instructions setting forth a method comprising the following: (a) providing a first and a second body fluid sample, wherein the first sample is taken from a subject from which status of osteoarthritis is to be determined and the second sample is taken from the same subject at a later time, and (b) detecting the amount of and determining the concentration of human collagen synthesis marker and collagen degradation marker in the first sample to provide a reference value, and detecting the amount of and determining the concentration of human collagen synthesis marker and collagen degradation marker in the second sample, wherein an increased concentration of human collagen degradation marker coupled with a decreased concentration of collagen synthesis marker in the second sample compared to the reference value indicates that the test subject has a high probability of having had or being at risk of progressive osteoarthritis.

Thus, based on the foregoing principles, this invention provides a method for quantitating the progress of osteoarthritis in a subject comprising the steps of: (a) detecting both a synthesis marker and degradation marker in a biological sample of the subject; (b) comparing the amounts of the synthesis marker and degradation marker; and (c) correlating the relative amounts of the synthesis marker and degradation marker with predetermined standards to quantitate the progress of osteoarthritis.

Further provided is a method for determining status of osteoarthritis in a patient comprising (a) assaying a sample taken from said patient for collagen synthesis markers and collagen degradation markers; and (b) comparing a value obtained in step (a) to a prior value obtained following assay of a prior sample taken from said patient, any difference there between being indicative of a change in the status of osteoarthritis in the patient.

These and other features, aspects and advantages of the present invention will become better understood with reference to the following description, examples and appended claims.

DETAILED DESCRIPTION OF THE INVENTION

Abbreviations and Definitions

Figure 1:
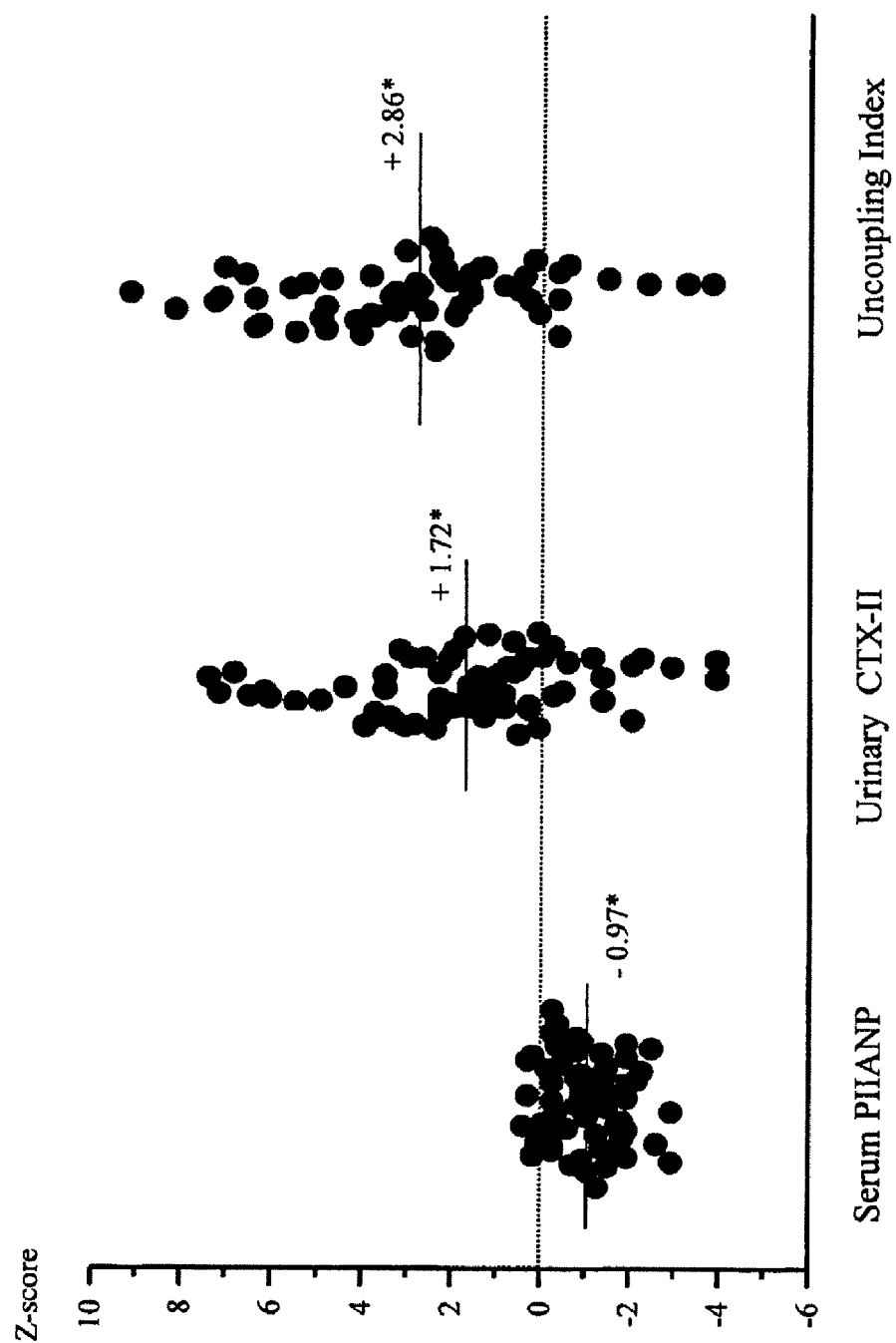
FIG. 1 is a graphical illustration of individual values of molecular markers of type II collagen metabolism in 75 patients with knee osteoarthritis.

Unless indicated otherwise, the terms defined below have the following meanings:

Therapeutic Treatment: As used herein, the term "therapeutic treatment" refers to receipt by a subject of a therapeutically effective amount of a pharmaceutical.

Therapeutically Effective Amount: As used herein, the term "therapeutically effective amount" refers to those amounts that, when administered to a particular subject in view of the nature and severity of that subject's disease or condition, will have the desired therapeutic effect, e.g., an amount which will cure, or at least partially arrest or prevent the disease or condition.

The Role of PIIANP and CTX-II in Cartilage Degeneration

Cartilage degeneration occurs in many diseases. Two of the most important cartilage degeneration conditions are OA and RA. The hallmark of OA is the loss of articular cartilage. This loss arises from an imbalance between cartilage synthesis and cartilage degradation over a variable period of time. Applicants have discovered that patients with knee OA are characterized by an uncoupling of type II collagen synthesis and degradation which can be detected by assays for serum PIIANP and urinary CTX-II. Combination of these two markers is useful in identifying patients with knee OA at high risk for rapid progression of joint damage, detecting changes in the progress of the disease and detecting OA inhibition over time using therapeutic agents, among other uses. The present methods and articles of manufacture are therefore useful as aids for diagnosing and monitoring cartilage degeneration in arthritic or pre-arthritic conditions such as osteoarthritis and rheumatoid arthritis, and also are useful as aids in determining the effectiveness of cartilage degeneration therapies, such as arthritis drugs and other therapies.

The present invention is supported by a seventy-five patient study of medial knee OA patients (51 women, 24 men; mean age: 63±8 years, mean disease duration: 4.3±1.5 years). At baseline, serum levels of N-propeptide of type IIA procollagen ("PIIANP") and urinary excretion of C-terminal cross-linking telopeptide of type II collagen ("CTX-II") as markers of type II collagen synthesis and degradation, were measured. Joint Space Width ("JSW") on X-ray and medial chondropathy by arthroscopy (Visual Analogue Scale ("VAS") score, 100 mm) were measured in all patients at baseline and in 52 of them after one year. Progression of joint destruction was defined by a decrease of JSW ±0.5 mm on X-ray and by an increase of chondropathy in VAS score >+8.0 units between the baseline and one year evaluation.

At baseline, patients with knee OA, compared to 58 healthy age and sex-matched controls, had decreased serum PIIANP (20 versus 29 ng/ml, $p<0.001$) and increased urinary CTX-II (618 versus 367 ng/mmol Cr, $p<0.001$). Highest discrimination between patients with OA and controls was obtained by combining PIIANP and CTX-II in an uncoupling index (Z-score CTX-II minus Z-score PIIANP) with a mean Z-score of +2.9 ($p<0.0001$). Increased baseline levels of uncoupling index was associated with greater progression of joint damage evaluated by either changes in JSW ($r=-0.46$, $p=0.0016$) or VAS score ($r=0.36$, $p=0.014$). Patients with both low PIIANP ($\leq$mean−1 Standard Deviation ("SD") of controls) and high CTX-II ($\geq$mean +1 SD of controls) progressed 8 fold more rapidly than the others ($p=0.012$ and $<0.0001$ when progression was assessed by X-ray and arthroscopy, respectively) and had a relative risk of progression of 2.9 (0.80–11.1) and 9.3 (2.9–39) for X-ray and arthroscopy, respectively.

The rate of type II collagen synthesis and degradation assessed by PIIANP and CTX-II was studied in patients with knee OA and to investigate whether the combined use of these two new molecular markers could predict the progression of joint damage evaluated by both X-ray and arthroscopy of the joints over one year. In this study, the two newly developed molecular markers of type II collagen metabolism provide evidence that patients with knee OA are characterized by an uncoupling of type II collagen synthesis and degradation. The combination of markers of synthesis and catabolism of type II collagen in an uncoupling index is highly predictive of the progression of joint damage suggesting that this index could be useful to identify patients at high risk for cartilage destruction. The methods and apparatus of the invention also allow accurate determination of the therapeutic effects of certain OA drug treatments, so are also useful for pharmaceutical efficacy studies in mammals. It will be understood by those skilled in the art that the methods and apparatus of the present invention can be used in a wide variety of mammalian subjects which include, but are not limited to, humans, rats, mice, rabbits, goats, and sheep. Other farm animals and companion animals such as horse, bovine, dogs and cats are also intended to be subjects of the present invention.

Cartilage degeneration can occur as a result of a variety of diseases, OA and RA being the primary diseases of interest. Those skilled in the art will understand that the methods and apparatus of the present invention may be used to predict and detect the progression of all arthritic conditions which result in cartilage degeneration. While the following study focuses on OA progression, the progression of other cartilage degeneration conditions such as RA and other arthritic conditions are not meant to be excluded from the scope of the present invention.

It was discovered that PIIANP is decreased compared to controls (Rousseau, supra) suggesting a deficit of type II collagen synthesis and thus of cartilage repair. However, decreased PIIANP levels measured alone in patients with knee OA cannot predict the progress of the disease. In contrast, the present invention shows that decreased serum PIIANP levels are associated when uncoupled with degradative markers with a faster rate of cartilage loss and alterations of type II collagen synthesis in the signal joint. No correlation between serum PIIANP and urinary CTX-II in patients with knee OA exists, suggesting that the rate of synthesis of type II collagen molecules is independent of the rate of degradation of resident molecules within cartilage matrix in favor of an uncoupling of these two activities. In addition, the combination of a marker of cartilage synthesis (PIIANP) with that of catabolism (CTX-II) in an uncoupling index allowed improvement of the discrimination between patients with knee OA and controls as compared with using one of these two markers alone.

These molecular markers may be used to identify patients at high risk for rapid progression of joint destruction who would benefit from chondroprotective therapy, as opposed to diagnosing OA. Indeed, clinical indices such as pain and physical function score are poorly related to the destruction of joint structure as is confirmed in Example 1 below that there was no association between pain, Lesquesne's functional index, knee effusion and progression. At baseline, it was found that a weak and non significant association between increased CTX-II levels and a lower joint space width in agreement with a previous cross-sectional study in patients with knee OA (Garnero, Ann. Rheum. Dis. 60, supra), whereas PIIANP was not predictive. These data suggest that levels of molecular markers are individually poorly predictive of the current extent of joint damage.

However, because molecular markers reflect dynamic changes in cartilage metabolism, they may be more predictive of the rate of cartilage loss in the following years. Longitudinal studies investigating the values of molecular markers to predict progression of joint damage are scarce. A predictive value of serum C-reactive protein (Spector, T. D., et al., *Low-levels increases in serum C-reactive protein are present in early osteoarthritis of the knee and predict progressive disease*, Arthritis Rheum. 40:723-727 (1997)), COMP (Sharif, M., et al., *Relationship between serum cartilage oligomeric matrix protein levels and disease progression in osteoarthritis of the knee joint*, Brit. J. Rheumatol. 34:306-310 (1995); Conrozier, T., et al., *Serum concentrations of cartilage oligomeric matrix protein and bone sialoprotein in hip osteoarthritis: A one year prospective study*, Ann. Rheum. Dis. 9:527-532 (1998)), and hyaluronic acid (Sharif, M., et al., *Serum hyaluronic acid level as a predictor of disease progression in osteoarthritis of the knee*, Arthritis Rheum. 38:760-767 (1995)), has been found in some but not all studies (Georges, C., et al., *Serum biologic markers as predictors of disease progression in osteoarthritis of the knee*, Arthritis Rheum. 40:590-591 (1997)). However molecular markers investigated in these previous studies were not specific of joint tissue (Garnero, Arthritis Rheum. 43, supra) and none of them evaluated the metabolism of type II collagen, the main abundant protein of cartilage matrix.

The Example shows that lower baseline levels of PIIANP and higher levels of CTX-II are associated with increased rate of progression of joint damage over one year evaluated either by X-rays or arthroscopy, in agreement with the concept that a decreased reparative process and increased degradation of cartilage matrix will lead to an accelerated rate of joint degradation. When used separately, the association between baseline levels of these two markers and progression was, however, modest and inconsistent across all analyses. In contrast, when PIIANP and CTX-II were combined in an uncoupling index of type II collagen synthesis and degradation, a highly significant correlation was found with progression of joint destruction assessed either by X-ray or arthroscopy. This index accounted for up to 21% of the inter-individual variability of the progression rate and each unit increase of this index was associated with 60 to 70% increase in the risk of progression. In addition, patients with both low levels of PIIANP and high CTX-II who accounted for about 29% of the population had a 3 to 9 fold increased risk of progression suggesting that this new index may indeed be an important new risk factor for progression of joint damage.

Therefore, using the two newly developed specific molecular markers can determine whether patients with knee OA are characterized by depressed type II collagen synthesis and increased type II collagen degradation. Combining these two molecular markers in an uncoupling index allows the identification of patients with a high risk of subsequent progression of joint damage.

The presence of PIIANP and CTX-II in the sample being tested can be detected by any means known to the art. For example, type IIA procollagen and/or propeptide can be identified in fluid samples using immunological techniques, or in tissue samples using immunohistochemical techniques. Alternatively, the peptides can be isolated, and sequenced. According to the invention, in preferred form, the biological sample is a fluid (e.g., serum, synovial fluid, or urine) from an adult human individual being tested, and the identifying agents are antibodies (polyclonal or monoclonal) which react with PIIANP and CTX-II proteins. Samples of cartilage for the assays can be obtained by arthroscopy of the joint or upon surgery.

Examples of degradation markers which can be used in the invention include COMP, keratin sulfate, link protein, aggrecan, aggrecan fragments, Type II collagen, and Type VI collagen, among other markers. These markers when measured individually have been attempted to be used to diagnose OA, but not the progression of the disease. The measurement of these markers can be analyzed by uncoupling methods with measurement of cartilage degradation markers, such as CTX-II, however, such that the progression of OA over the course of time may be predicted.

Immunoassays

Antibodies of this invention can be used as probes in detecting certain antigens in human joints. The expression or lack of expression of these antigens can provide clinically exploitable information which is not apparent after standard histopathological evaluations. It is then possible to correlate the phenotypes of individual joint conditions, OA in particular, with various aspects of joint condition and responsiveness to certain types of therapies, thus establishing important classifications of prognosis.

Standard methods using antibodies can be used to detect and quantitate collagen synthesis and degradation markers including, but not limited to, radioimmunoassays ("RIA"), receptor assays, enzyme immunoassays ("EIA"), cytochemical bioassays, ligand assays, immunoradiometric assays, fluoroimmunoassays, and enzyme-linked immunosorbent assays ("ELISA"). Particularly preferred, for ease of detection, and its quantitative nature, is the sandwich or double antibody assay, of which a number of variations exist, all of which are intended to be encompassed by the present invention. These methods are well known and will be understood by those skilled in the art to require a reasonable amount of experimentation to optimize the interaction between antibodies and antigens and the detection of the antigens by the antibodies. These and other immunoassay techniques may be found in PRINCIPLES AND PRACTICE OF IMMUNOASSAY, 2ND EDITION, Price and Newman, eds., MacMillan (1997) and ANTIBODIES, A LABORATORY MANUAL, Harlow and Lane, eds., Cold Spring Harbor Laboratory, Ch. 9 (1988), each of which is incorporated herein by reference in its entirety.

The use of antibodies described herein can be used to screen human biological fluids for the presence of a specific antigen, preferably collagen synthesis and degradation markers. In vitro immunoserological evaluation of sera withdrawn from patients thereby permits non-invasive determination of the progression of cartilage degeneration. By way of illustration, human fluids, such as blood serum or urine, can be taken from a patient and assayed for a specific epitope, either as released antigen or membrane-bound on cells in the sample fluid, using the anti-marker antibodies in standard RIAs or ELISAs known in the art. The antibodies used in such methods are preferably monoclonal antibodies.

Particularly preferred, for ease of detection and because of its quantitative nature, is the sandwich or double antibody assay of which a number of variations exist, all of which are intended to be encompassed by the present invention. For example, in a typical forward sandwich assay, unlabeled antibody is immobilized on a solid substrate, e.g., microtiter plate wells, and the sample to be tested is brought into contact with the bound molecule. After incubation for a period of time sufficient to allow formation of an antibody-antigen binary complex, a second antibody labeled with a reporter molecule capable of inducing a detectable signal is then added. Incubation is continued allowing sufficient time for binding with the antigen at a different site and the formation of a ternary complex of antibody-antigen-labeled antibody. Any unreacted material is washed away, and the presence of the antigen is determined by observation of a signal which may be quantitated by comparison with a control sample containing known amounts of antigen. Variations on the forward sandwich assay include the simultaneous assay in which both sample and antibody are added simultaneously to the bound antibody, or a reverse sandwich assay in which the labeled antibody and sample to be tested are first combined, incubated and added to the unlabelled surface bound antibody. These techniques are well known to those skilled in the art, and the possibility of minor variations will be readily apparent. As used herein, the term "sandwich assay" is intended to encompass all variations on the basic two-site technique.

One limiting factor of the sandwich assays techniques of the present invention requires that both antibodies have different binding specificities for the collagen synthesis and degradation markers. Thus, a number of possible combinations are possible. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art.

Following binding, the solid phase-antibody complex is washed in preparation for the test sample. An aliquot of the body fluid containing the collagen synthesis and degradation markers to be tested is then added to the solid phase complex and incubated at 25° C. for a period of time sufficient to allow binding of any collagen synthesis or degradation marker present to the antibody specific for collagen synthesis or degradation marker. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. The term "reporter molecule" as used in the present invention is meant a molecule which by its chemical nature provides an analytically detectable signal which allows the detection of antigen-bound antibody. Detection must be at least relatively quantifiable to allow determination of the amount of antigen in the sample. The signal may be calculated in absolute terms or may be calculated in comparison with a standard (or series of standards) containing a known normal level of antigen.

The most commonly used reporter molecules of this type of assay are either enzymes or fluorophores. In the case of an EIA, an enzyme is conjugated to the second antibody, often by means of glutaraldehyde or periodate. As will be apparent to those skilled in the art, a wide variety of different conjugation techniques exist. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates which yield a fluorescent product rather than the chromogenic substrates noted above. In all cases, the enzyme-labeled antibody is added to the first antibody-synthesis marker or antibody-degradation marker complex and allowed to bind to the complex, then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen which is present in the serum sample.

Alternatively, fluorescent compounds such as fluorescein or rhodamine may be chemically coupled to antibodies without altering their binding capacity. When activated by illumination with light of a particular wavelength, the fluorochrome-labeled antibody absorbs the light energy inducing a state of excitability in the molecule followed by emission of the light at a longer wavelength. The emission appears as a characteristic color visually detectable with a light microscope. As in the EIA, the fluorescent-labeled antibody is allowed to bind to the first antibody-synthesis marker or antibody-degradation marker complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to those skilled in the art how to vary the procedure to suit the required use.

In yet another alternative embodiment, the human sample to be tested which contains the collagen synthesis or degradation markers may be used in a single site immunoassay wherein it is adhered to a solid substrate either covalently or noncovalently. An unlabeled anti-synthesis marker or anti-degradation marker antibody is brought into contact with the sample bound on the solid substrate. After a suitable period of incubation sufficient to allow formation of an antibody-antigen binary complex, a second antibody, labeled with a reporter molecule capable of inducing a detectable signal is added and incubation is continued allowing sufficient time for the formation of a ternary complex of antigen-antibody-labeled antibody. For the single site immunoassay, the second antibody may be a general antibody, i.e., zenogeneic antibody to immunoglobulin, particularly anti-(IgM and IgG) linked to a reporter molecule, that is capable of binding an antibody that is specific for the synthesis marker or degradation marker of interest.

In a competitive ELISA, a patient serum and an antigen-specific conjugate are co-incubated with a captured antigen.

The amount of color developed is inversely proportional to the amount of antigen-specific patient immunoglobulin present. Careful standardization is required to interpret the results. These and other immunoassays are within the scope of the presentation.

Histological Techniques

Antibodies against collagen synthesis and degradation markers can also be used to detect collagen synthesis and degradation markers in histological and cytological specimens, and in particular, to determine the progression of cartilage degeneration based on staining patterns and intensities. For example, staining patterns can be observed by using an immunostaining technique and monoclonal antibodies against chondrocyte or other joint cells or tissues with a small degree of heterogeneity. Using this method, morphologically osteoarthritic cells can generally be seen to exhibit an increased degree of staining when compared to non-osteoarthritic cells. Non-specific staining will preferably be absent on non-collagen or other cartilage components not affected by cartilage degeneration of the joint specimen.

Immunofluorescent histological techniques can also be used to examine human specimens with monoclonal antibodies. In a typical protocol, slides containing cryostat sections of frozen, unfixed tissue biopsy samples or cytological smears are air dried, formalin fixed and incubated with the monoclonal antibody preparation in a humidified chamber at room temperature. The slides are then layered with a preparation of antibody directed against the monoclonal antibody, usually some type of anti-mouse immunoglobulin if the monoclonal antibodies used are derived from the fusion of a mouse spleen lymphocyte and a mouse myeloma cell line. This antimouse immunoglobulin is tagged with a compound that fluoresces at a particular wavelength, e.g., rhodamine or fluorescein isothiocyanate. The staining pattern and intensities within the sample are then determined by fluorescent light microscopy and optionally photographically recorded. See Aigner, et al., supra for a discussion of histological methods which may be used within the scope of the present invention.

Monoclonal Antibodies

Monoclonal antibodies which can be used in the invention can be produced by a hybridoma using methods well known in the art. Various additional procedures known in the art may be used for the production of antibodies to epitopes of the collagen synthesis and degradation markers. Such antibodies include but are not limited to polyclonal, monoclonal, chimeric, single chain, Fab fragments and a Fab expression library. For the production of antibodies, various host animals may be immunized by injection with a particular collagen synthesis or degradation marker, or a synthetic collagen synthesis or degradation marker, including but not limited to rabbits, mice, rats, goats, horses, pigs, among other animals. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *corynebacterium parvum*.

Monoclonal antibodies to peptides of collagen synthesis and degradation markers may be prepared by using any technique which provides for the production of antibody molecules by continuous cell lines in culture. These include, but are not limited to the hybridoma technique originally described by Kohler and Milstein, (Nature, 256:495-497 (1975)). Monoclonal antibodies specific to collagen synthesis and degradation markers may be produced in germ-free animals utilizing recent technology (PCT/US90/02545). Human antibodies may be used and can be obtained by using human hybridomas (Cote, et al., Proc. Natl. Acad. Sci., 80:2026-2030 (1983)) or by transforming human B cells with EBV virus in vitro (Cole, et al., In: MONOCLONAL ANTIBODIES AND CANCER THERAPY, Alan R. Liss, pp. 77-96 (1985)). In addition, techniques developed for the production of chimeric antibodies by splicing the genes from a mouse antibody molecule of appropriate antigen specificity together with genes from a human antibody molecule of appropriate biological activity can be used (Morrison, et al., Proc. Natl. Acad. Sci., 8(1): 6851-6855 (1984); Neuberger, et al., Nature, 312:604-608 (1984); Takeda, et al., Nature, 314:452-454 (1985))

Monoclonal or polyclonal antibodies specific for the substrate of interest which may advantageously be used as anchoring antibodies should be prepared against unique epitopes of the substrate to minimize cross reactions with other substrates. Similarly, the detection antibody should only react with a collagen synthesis or degradation marker. Monoclonal antibodies or polyclonal antibodies with high binding affinities for such unique epitopes may be used, preferably those that will not interfere with ligand binding if the substrate is also a receptor. For example, where the substrate is a receptor involved in signal transduction, the extracellular domain, which bears unique epitopes that may be involved in ligand recognition and binding, may advantageously be used as the immunogen. For non-receptor substrates where the amino acid sequence is known, non-conserved, variable regions of the protein may be used as immunogens.

Solid Phase Systems

The solid phase used in the assays of this invention may be any surface commonly used in immunoassays. For example, the solid phase may be particulate; it may be the surface of beads, for example, glass or polystyrene beads; or it may be the solid wall surface of any of a variety of containers, for example, centrifuge tubes, columns, microtiter plate wells, filters, membranes and tubing, among other containers. The invention also includes solid supports which may be attached to the surface of a surgical device or other instrument which directly contacts fluid to be studied while the instrument is within a patient. The fluid in direct contact with the instrument may be in the joint, blood stream or other tissue which contains collagen synthesis or degradation markers.

When particles are used as the solid phase, they will preferably be of a size in the range of from about 0.4 to 200 microns, more usually from about 0.8 to 4.0 microns. Magnetic or magnetizable particles such as, paramagnetic particles (PMP), are a preferred particulate solid phase, and microtiter plate wells are a preferred solid wall surface. Magnetic or magnetizable particles may be particularly preferred when the steps of the methods of this invention are performed in an automated immunoassay system.

Preferred detection/quantitation systems of this invention may be luminescent, and a luminescent detection/quantitation system in conjunction with a signal amplification system could be used, if necessary. Exemplary luminescent labels, preferably chemiluminescent labels, are detailed below, as are signal amplification systems.

Signal Detection/Quantitation Systems

The complexes formed by the assays of this invention can be detected, or detected and quantitated, by any known detection/quantitation systems used in immunoassays. As appropriate, the antibodies of this invention used as tracers may be labeled in any manner directly or indirectly that results in a signal that is visible or can be rendered visible.

Detectable marker substances include radionuclides, such as $^3$H, $^{125}$I, and $^{131}$I; fluorescers, such as, fluorescein isothiocyanate and other fluorochromes, phycobiliproteins, phycoerythin, rare earth chelates, Texas red, dansyl and rhodamine; colorimetric reagents (chromogens); electron-opaque materials, such as colloidal gold; bioluminescers; chemiluminescers; dyes; enzymes, such as, horseradish peroxidase, alkaline phosphatase, glucose oxidase, glucose-6-phosphate dehydrogenase, acetylcholinesterase, α-, β-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immunocomplex formed. Exemplary of enzyme substrate combinations are horseradish peroxidase and tetramethyl benzidine (TMB), and alkaline phosphatase and paranitrophenyl phosphate (pNPP).

Preferred detection, or detection and quantitation systems according to this invention produce luminescent signals, bioluminescent (BL) or chemiluminescent (CL). In BL or CL assays, the intensity or the total light emission is measured and related to the concentration of the analyte. Light can be measured quantitatively using a luminometer (photomultiplier tube as the detector) or charge-coupled device, or qualitatively by means of photographic or X-ray film. The main advantage of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, *Vargulla* and *Renilla*. Luminol can be used optionally with an enhancer molecule, preferably selected from the group consisting of 4-iodophenol or 4-hydroxycinnamic acid. Acridinium esters are one of the preferred types of CL labels according to this invention. A signal is generated by treatment with an oxidant under basic conditions.

Also preferred luminescent detection systems are those wherein the signal is produced by an enzymatic reaction upon a substrate. BL and CL detection schemes have been developed for assaying alkaline phosphatase (AP), glucose oxidase, glucose 6-phosphate dehydrogenase, horseradish peroxidase (HRP), and xanthine-oxidase labels, among others. AP and HRP are two preferred enzyme labels which can be quantitated by a range of BL and CL reactions. For example, AP can be used with a substrate, such as an adamantyl 1,2-dioxetane aryl phosphate substrate (e.g., AMPPD or CSPD; (Kricka, L. J., "Chemiluminescence and Bioluminescence, Analysis by," at p. 167, Molecular Biology and Biotechnology: A Comprehensive Desk Reference, ed. R. A. Meyers, VCH Publishers; N.Y., N.Y.; 1995)); preferably a disodium salt of 4-methoxy-4-(3-phosphatephenyl)spiro [1,2-dioxetane-3,2'-adamantane], with or without an enhancer molecule, preferably, 1-(trioctylphosphonium methyl)-4-(tributylphosphonium methyl)benzene diochloride. HRP is preferably used with substrates, such as, 2',3',6'-trifluorophenyl 3-methoxy-10-methylacridan-9-carboxylate.

BL and CL reactions can also be adapted for analysis of not only enzymes, but other substrates, cofactors, inhibitors, metal ions and the like. For example, luminol, firefly luciferase, and marine bacterial luciferase reactions are indicator reactions for the production or consumption of peroxide, ATP, and NADPH, respectively. They can be coupled to other reactions involving oxidases, kinases, and dehydrogenases, and can be used to measure any component of the coupled reaction (enzyme, substrate, cofactor).

The detectable marker may be directly or indirectly linked to an antibody used in an assay of this invention. Exemplary of an indirect linkage of the detectable label is the use of a binding pair between the antibody and the marker, or the use of well known signal amplification signals, such as, using a biotinylated antibody complexed to UGP and then adding streptavidin conjugated to HRP and then TMB.

Exemplary of binding pairs that can be used to link antibodies of assays of this invention to detectable markers are biotin/avidin, streptavidin, or anti-biotin; avidin/anti-avidin; thyroxine/thyroxine-binding globulin; antigen/antibody; antibody/anti-antibody; carbohydrate/lectins; hapten/anti-hapten antibody; dyes and hydrophobic molecules/hydrophobic protein binding sites; enzyme inhibitor, coenzyme or cofactor/enzyme; polynucleic acid/homologous polynucleic acid sequence; fluorescein/anti-fluorescein; dinitrophenol/anti-dinitrophenol; vitamin B12/intrinsic factor; cortisone, cortisol/cortisol binding protein; and ligands for specific receptor protein/membrane associated specific receptor proteins. Preferred binding pairs according to this invention are biotin/avidin or streptavidin, more preferably biotin/streptavidin.

Various means for linking labels directly or indirectly to antibodies are known in the art. For example, labels nay be bound either covalently or non-covalently. Exemplary antibody conjugation methods are described in: Avarmeas, et al., Scan. J. Immunol., 8 (Suppl. 7):7 (1978); Bayer, et al., Meth. Enzymol., 62:308 (1979); Chandler, et al., J. Immunol. Meth., 53:187 (1982); Ekeke and Abuknesha, J. Steroid Biochem., 11:1579 (1979); Engvall and Perlmann, J. Immunol., 109:129 (1972); Geoghegan, et al., Immunol. Comm., 7:1 (1978); and Wilson and Nakane, Immunofluorescence and Related Techniques, p. 215 (Elsevier/North Holland Biomedical Press; Amsterdam (1978)).

Depending upon the nature of the label, various techniques can be employed for detecting, or detecting and quantitating the label. For fluorescers, a large number of fluorometers are available. For chemiluminescers, luminometers or films are available. With enzymes, a fluorescent, chemiluminescent, or colored product can be determined or measured fluorometrically, luminometrically, spectrophotometrically or visually.

Automated Immunoassay System

The methods of this invention can be readily adapted to automated immunochemistry analyzers. To facilitate automation of the methods of this invention and to reduce the turnaround time, anti-UGP antibodies may be coupled to magnetizable particles.

A preferred automated/immunoassay system is the Ciba Corning ACS:180™ Automated Chemiluminescence System (CCD; Medfield, Mass. (USA)). The Ciba Corning ACS: 180™ Automated Immunoassay System is described in Dudley, B. S., J. Clin. Immunoassay. 14(2):77 (Summer 1991). The system uses chemiluminescent labels as tracers and paramagnetic particles as solid-phase reagents. The ACS:180 system accommodates both competitive binding and sandwich-type assays, wherein each of the steps are automated. The ACS:180 uses micron-sized paramagnetic particles that maximize the available surface area, and provide a means of rapid magnetic separation of bound tracer from unbound tracer without centrifugation. Reagents can be added simultaneously or sequentially. Other tags, such as an enzymatic tag, can be used in place of a chemiluminescent label, such as, acridinium ester.

Assays of Urine

The assays of the present invention may also be adapted to a "dip stick" format according to U.S. Pat. Nos. 6,352,862 and 5,602,040, each of which is incorporated herein by reference in its entirety, or similar apparatus.

Assays of Whole Blood

The assays of the present invention may also be adapted to a "dip stick" format according the U.S. Reissue Pat. No. RE035306, incorporated herein by reference in its entirety, or similar apparatus.

Kits

Further, the present invention provides a kit for detecting cartilage degeneration status, such as the progression of cartilage degeneration, which is applicable for the practice of the method of the present invention.

The kit comprises an antibody specific to collagen synthesis and degradation markers, whereby the detection of cartilage degeneration and other cartilage degeneration conditions can be carried out using the antibody in an immunological assay. When a two antibody sandwich ELISA is employed as the immunological assay, the kit may comprise first and second antibodies specific to collagen synthesis and degradation markers. The second antibody is preferably capable of binding to a conjugate of the collagen synthesis and degradation markers and the first antibody. For this purpose, for example, an antibody that recognizes an epitope different from that recognized by the first antibody may be used as the second antibody. It is preferable that the first and second antibodies be monoclonal antibodies.

The kit of the present invention may further comprise a substance and/or a device suitable for the detection of antibodies, the immobilization of antibodies, and the like. To immobilize the antibodies, the kit may further comprise a carrier (e.g., a microtiter plate), a solution for the immobilization (e.g., carbonate buffer) and a blocking solution (e.g., gelatin-containing PBS). For the detection of the antibodies, it is preferable that the antibodies be labeled previously. In this case, the kit may further comprise a detecting reagent for detecting the label. For example, when biotin is used as the labeling substance, the detecting reagent may comprise a conjugate of streptavidin with horseradish peroxidase (HRP) as well as a color-developing solution that is capable of developing a color by the action of HRP.

In one embodiment, the kit will include instructions setting forth at least that (a) a first and a second body fluid sample are to be provided, wherein the first sample is taken from a subject from which status of osteoarthritis is to be determined, and the second sample is taken from the same subject at a later time, and (b) the amount of, and the concentration of the human collagen synthesis marker and of the collagen degradation marker in the first sample are detected to provide a reference value, and the amount of and concentration of the human collagen synthesis marker and of the collagen degradation marker in the second sample are detected, wherein an increased concentration of human collagen degradation marker coupled with a decreased concentration of collagen synthesis marker in the second sample compared to the reference value indicates that the test subject has a high probability of having had or being at risk of progressive osteoarthritis.

These and other features, aspects and advantages of the present invention will become better understood with reference to the following description, examples and appended claims.

EXAMPLE

The following experimental example describing evaluation of subjects exhibiting OA symptoms is offered by way of illustration and not by way of limitation.

Patients with Knee Osteoarthritis and Healthy Controls 75 patients (51 women, 24 men; mean age: 63.0±8.0 years) were investigated who met the American College of Rheumatology criteria for primary knee OA (Altman, R., et al., Development of criteria for the classification and reporting of osteoarthritis. Classification of osteoarthritis of the knee. Diagnostic and Therapeutic Criteria Committee of the American Rheumatism Association, Arthritis Rheum. 29:1039-49 (1986)). These patients were part of two larger randomized, multicenter, double blind studies comparing the efficacy of diacerhein and Tenidap and including respectively 61 and 665 patients (Ayral, X., et al., Abstract, Progression of knee osteoarthritis assessed by arthroscopy: a multicenter, randomized, double blind comparison of tenidap sodium versus piroxicam, Ann. Rheum. Dis. 59 (supp.):S54 (2000)). Other inclusion criteria were: 1) clinical involvement (pain) of the medial femorotibial compartment, 2) active disease defined by pain of any duration in the signal knee on at least 30 days in the last 2 months and by inadequate pain control certified by prior failure of intra-articular glucocorticoid injection, physical exercises, analgesics and non steroidal anti-inflammatory drugs, and justifying joint lavage, 3) absence of advanced disease defined by a radiological joint space width of 2 mm or greater at the narrowest point of the medial femorotibial compartment of the signal joint on weight-bearing radiographs with knees fully extended, 4) presence of chondropathy of the medial compartment at entry which was approved by the central reader of video made during the arthroscopy screening. For approval, at least 10% of one articular surface of the medial compartment (femoral condyle or tibial plateau) had to be affected by superficial fibrillation or worse and if 90% or greater of both surfaces showed absence of cartilage, the patient was not eligible, 5) no intra-articular lesion requiring surgery (e.g. of meniscus, cartilage or ligament) at the arthroscopy screening or likely to require surgery during study period, 6) no intra-articular injection within the 3 months prior to the arthroscopy screening and 7) absence of contraindication of arthroscopy (anticoagulant therapy, cutaneous lesion of the knee, allergy to lidocaine).

All women were postmenopausal and all patients were without treatments that could interfere with bone metabolism including estrogen replacement. Fifty two of these 75 patients were evaluated after one year for progression of joint destruction assessed by both X-ray and arthroscopy.

Healthy subjects included 38 postmenopausal women (mean age: 63.2±8.1 years from 50 to 80 years) and 20 men aged from 53 to 79 years (mean; 62±8.2 years). Menopausal status was defined as the absence of menses for at least 12 months. Healthy women and men were randomly selected from two large population based-cohorts involved in prospective studies on the determinants of bone loss in women (OFELY study) and men (MINOS study) (Garnero, E., et al., Increased bone turnover in late postmenopausal women is a major determinant of osteoporosis, J. Bone Miner. Res. 11:337-349 (1996); Szulc, P., et al., Cross-sectional assessment of age-related bone loss in men: The MINOS Study, Bone 26:123-129 (2000)). The cohort of the OFELY study comprises 1039 healthy female volunteers, 31-89 years of age randomly selected from affiliates of the section of a health insurance company (Mutuelle Générale de l'Education Nationale) from the Rhône district in France. The cohort of the MINOS study comprises 842 healthy male volunteers, 50-85 years of age, randomly selected from the affiliated of the section of a health insurance company (Société de Secours Minière de Bourgogne) in Montceau les Mines, a town located in the same region as that of the healthy women. All healthy women and men did not have evidence of symptomatic OA as assessed by clinical examination of the hands performed by an experienced rheumatologist and by using the following question: "Has a doctor ever told you that you had osteoarthritis". Furthermore, X-ray films of the thoracic and lumbar spine were obtained in all subjects. Spine films were graded with a standard atlas to document the severity of disc degeneration and osteophyte formation using the method of Lane, et al. (Reliability of new indices of radiographic osteoarthritis of the hand and hip and lumbar spine degeneration, J. Rheumatol. 20:1911-1918 (1993)) with a grade of 0 as normal, 1 for mild narrowing and or mild osteophytes, 2 moderate-severe (2-3) narrowing and or moderate-severe (2-3) osteophytes. Subjects with a grade of 2 (moderate-severe) were excluded from the control group. All subjects were healthy without any disease or treatment that could interfere with bone or joint metabolism including hormone replacement therapy in postmenopausal women.

This prospective, longitudinal study of one-year duration was approved by the local ethical committee and informed consent was obtained from all patients.

Clinical Variables

At baseline, pain was evaluated in all patients using a 100 mm visual analogue scale (VAS), functional disability was assessed by the Lequesne's functional index (Lequesne, M., et al., Indexes of severity for osteoarthritis of the hip and knee. Validation-value in comparison with other assessment tests, Scand. J. Rheumatol. 85 (supp. 65):85-89 (2000)), disease duration and presence or absence of knee effusion were collected. Additionally the presence of concomitant osteoarthritis affected joints was evaluated using the articular index whose numerical value is the sum of the total cartilage surface area (as $cm^2$) of each symptomatic joint as previously reported (Goldberg, R. L., et al., Elevated plasma levels of hyaluronate in patients with osteoarthritis and rheumatoid arthritis, Arthritis Rheum. 34:799-806 (1991)).

Radiological Variables

Radiological evaluation consisted of bilateral anteroposterior weight-bearing knee radiographs with the knee fully extended. Radiographs were taken in a single radiography unit by the same staff of 3 technicians using a standardized technique: 1) patient positioning: patients stand with knees fully extended, weight equally distributed on both legs, back of knees in contact with the cassette, feet rotated so that tibial spines are centralized in femoral notch, 2) radiographic procedure: both knees are X-rayed together, the X-ray beam is directed at center of the medial compartment of the signal knee and with the aid of fluoroscopy the beam is placed parallel to the medial tibial plateau with a tube to film distance of 1.10 m. The same procedure was followed for the second X-ray after 12 months.

The severity of OA of the medial femorotibial compartment was evaluated by measuring the joint space width, i.e., the inter-bone distance between the medial femoral condyle and the medial tibial plateau at the narrowest point in millimeters (Ravaud, supra). The paired radiographs of each patient at entry and after one year were analyzed by a single investigator using a blind procedure in which the investigator was unaware of patient identity and of the chronology of the radiographs.

Arthroscopy of the Knees

Arthroscopy of the knee was performed under local anaesthesia, without tourniquet hemostasis, with a 2.7 mm Storz Arthroscope (Storz, Paris, France) having a 30° fore oblique lens, using inferolateral approach. Arthroscopic exploration was combined with joint lavage, consisting of 1 liter of normal saline. The arthroscopic evaluation focused on the symptomatic compartment, i.e., the medial femorotibial compartment. Each arthroscopy was: recorded on a VHS videotape (Sony, Tokyo, Japan). Arthroscopies were performed by 3 trained arthroscopists and recorded on the same planned, systematic, standardized manner. All videotapes were analyzed. Arthroscopies were scored for chondropathy using the overall assessment of the investigator by a 100 mm VAS in which 0 indicates the absence of chondropathy and 100 the most severe chondropathy as previously reported (Ayral, Semin. Arthritis Rheum. 22, supra). One VAS is used for each articular surface of the medial compartment: medial femoral condyle and medial tibial plateau. A VAS score is obtained by averaging the VAS scores from the two corresponding articular surfaces of the compartment. The paired arthroscopy videotapes of each patient at entry and after one year were analyzed, using a blind procedure in which the investigator was unaware of patient identity and of the chronology of the videotapes.

Biochemical Measurements

Fasting blood samples were collected before 10:00 a.m. in plain tubes containing separation gel. They were allowed to stand for 20 minutes and then centrifuged for 10 minutes at 2500 rpm. The serum was then mixed and split in different aliquots. The interval between blood drawing and freezing at −70° C. was less than 2 hours. Fasting second morning void urine samples were also collected in plastic containers. After mixing the whole collection, aliquots of urine were transferred into plastic tubes and frozen at −70° C. without any acidification.

Both serum and urine samples were obtained in all OA patients on the day pain and function were assessed, the radiographs were taken and arthroscopy performed. Samples were obtained before arthroscopic exploration. Samples were obtained in controls according to the same procedure. All biological samples were kept frozen at −70° C. until assayed.

Molecular Marker of Type II Collagen Synthesis

Synthesis of type II collagen was evaluated by measuring serum PIIANP using a recently developed ELISA (Rousseau, supra). This ELISA is based on a rabbit polyclonal antiserum raised against the recombinant human GST-exon 2 fusion protein (Oganesian, supra) and recombinant human GST-exon 2 as a standard. The specificity of the antibody against PIIANP was previously demonstrated by Western blot analyses against the recombinant exon 2 protein (prior and after cleavage with thrombin) and against type IIA procollagen isolated from the culture medium of human fetal ribs (Oganesian, supra). Briefly, microtiter plates are coated overnight at 4° C. with 100 µl (10 ng/ml) of GST-exon 2 protein and then saturated for 2 hours at room temperature with phosphate buffer saline, 1% bovine serum albumin (Sigma, St Louis, Mo.). After washing, 100 µl of standards or serum samples are incubated for 4 hours at room temperature together with 100 µl of anti-GST-exon 2 antiserum at the adequate dilution (1/1650). After washing, 100 µl of a peroxydase conjugated anti-rabbit antibody (Sigma, St Louis, Mo.) is added into each well and incubated for 1 hour at room temperature. After washing, 100 µl of $H_2O_2$/tetramethylbenzidine substrate indicator solution (Sigma, St Louis, Mo.) are added into each well. After 30 minutes of incubation at room temperature, 100 µl of stopping solution (2M $H_2SO_4$) are pipetted into each well. The absorbency at 450 nm is measured in an ELISA plate reader, and the concentration of the unknown samples is determined by constructing a standard curve from measurement of the standards with known concentrations of human recombinant exon-2 protein. Intra and interassay CVs are lower than 11% (Rousseau, supra).

Molecular Marker of Type II Collagen Degradation

Type II collagen degradation was assessed by measuring urinary C-terminal cross-linking telopeptide of type II collagen (U-CTX-II) using an ELISA based on a monoclonal antibody raised against a linear six amino acid epitope of the type II collagen C-telopeptide (Christgau, supra). Intra and inter assay CVs are lower than 8% and 10%, respectively (Christgau, supra).

Statistical Analyses

All data are expressed in mean ±SD unless otherwise specified. Distribution of serum PIIANP and urinary CTX-II data in controls and patients with knee OA was assessed by the Shapiro-Wilk test. Serum PIIANP levels were normally distributed in both controls and OA patients (p=0.89 and 0.19 in controls and knee OA patients, respectively). Urinary CTX-II levels were normally distributed in controls (p=0.65), but not in knee OA patients (p<0.0001). Consequently, urinary CTX-II levels were log transformed before analyses which resulted in normalization of the data (p=0.51 and p=0.24, in controls and knee OA patients respectively). To compare the performance of the molecular markers to differentiate patients with knee OA from controls, data was expressed as a Z-score, i.e., number of SDs from the mean of age-matched healthy controls using log-transformed data. An uncoupling index of type II collagen synthesis and degradation (Z score CTX-II minus Z-score PIIANP) was calculated as suggested by Eastell and colleagues (Eastell, R., et al., Evaluation of bone turnover in type I osteoporosis using biochemical markers specific for both bone formation and bone resorption, Osteoporos Int. 3:255-260 (1993)) for biochemical markers of bone turnover in osteoporosis. Such biochemical markers of bone turnover in osteoporosis are unassociated with the biochemical markers of the present invention related to collagen synthesis and degradation in osteoarthritis and other cartilage degeneration conditions.

Radiological progression of joint destruction was defined as an increase in the joint space narrowing (JSN) of 0.5 mm and more between baseline and 12 months. This cut-off is based on the intra-observer reproducibility of radiographic measurement over 2 weeks (Ravaud, supra) and calculated according to the method proposed by Bland and Altman (Bland, J. M., et al., Statistical methods for assessing agreement between two methods of clinical measurement, Lancet i:307-310 (1986)). Arthroscopic progression of chondropathy was defined as an increase in the VAS score of more than 8.0 units between baseline and 12 months. This cut-off is based on the intra-observer reproducibility of the arthroscopic quantification of chondropathy, as previously reported (Ayral, J. Rheumatol. 23, supra). Differences in serum PIIANP, urinary CTX-II and uncoupling index between progressors and non-progressors were assessed by unpaired student t-test. Correlation between Z-score of PIIANP, Z-score of urinary CTX-II, the uncoupling index and radiological or arthroscopic progression was assessed by linear regression analyses. Patients were also separated according to baseline levels of serum PIIANP and urinary CTX-II using as a cut-off the mean −1 SD (serum PIIANP) and the mean +1 SD (urinary CTX-II) of healthy controls. For CTX-II we also defined patients at risk as those with values above the mean +2 SDs of the controls in order to identify a proportion of patients at risk similar to those identified by serum PIIANP. The risk of radiological and arthroscopic progression of joint destruction according to baseline levels of molecular markers was estimated by relative risks obtained by logistic regression analyses.

All statistical analyses were carried out using SAS (SAS institute Inc., Cary, N.C.) (SAS STAT User's Guide, Version 6, 4$^{th}$ Ed, Vols. 1 and 2).

RESULTS

Type II Collagen Synthesis and Degradation in Patients with Knee OA and in Healthy Controls As shown on Table 1, patients with knee OA and controls did not differ for gender, age and height. As expected patients with knee OA were heavier and had a higher body mass index (BMI) than controls. In the whole population, however, there was no significant association between serum PIIANP and urinary CTX-II with either body weight (p=0.69 and 0.21, for serum PIIANP and urinary CTX-II, respectively) or BMI (p=0.62 and 0.77). Patients with knee OA had decreased serum PIIANP levels (20.2±5.8 versus 28.5±5.1 ng/ml, p<0.001, in knee OA patients and controls, respectively) and increased urinary excretion of CTX-II (618±389 versus 367±88 ng/mmol Cr, p<0.001) compared to age-matched controls.

FIG. 1 is a is graphical illustration of individual values of molecular markers of type II collagen metabolism in 75 patients with knee osteoarthritis. Each value is expressed as a Z-score, i.e. in number of standard deviations from the mean of 58 healthy age-matched controls. The plain lines and associated number represent the mean Z-score. The asterisks (*) represent the statistical significance (p<0.0001) of the mean Z-score compared to the value of 0 as assessed by one group t-test. PIIANP refers to N-propeptide of type IIA procollagen, and CTX-II refers to C-terminal cross-linking telopeptide of type II collagen. Uncoupling index was calculated as the Z-score of urinary CTX-II minus Z-score of serum PIIANP.

When expressed as a Z-score, urinary CTX-II was more sensitive than serum PIIANP (p<0.001) to discriminate knee OA patients from healthy controls (FIG. 1). No significant correlation (r=−0.068, p=0.60) was found between serum PIIANP and urinary CTX-II and the highest discrimination between OA patients and controls was obtained when CTX-II and PIIANP were combined in an uncoupling index of type II collagen synthesis and degradation (Z-score CTX-II minus Z-score PIIANP) with a mean Z-score of +2.9 (p<0.001 versus Z-score of CTX-II and PIIANP) (FIG. 1).

At baseline, it was found that a weak association between the Z-score of urinary CTX-II and joint space width (r=−0.16, p=0.17) and between the uncoupling index and Lesquesne's functional index (r=0.25, p=0.05). None of the other associations between the Z-score of PIIANP or CTX-II and indices of pain, function or joint damage were significant.

Figure 2:
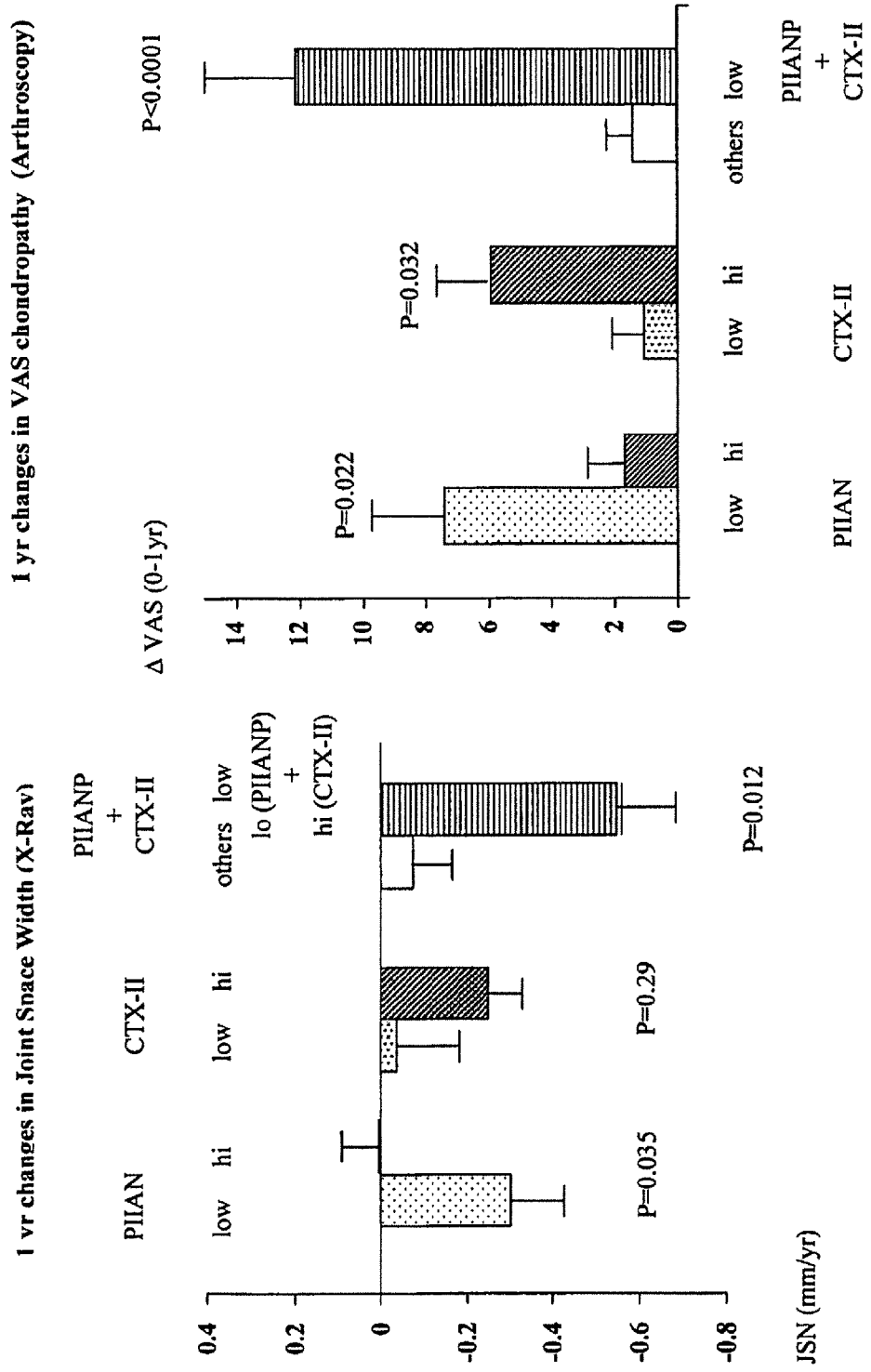
FIG. 2 shows graphical illustrations of progression of joint damage over one year in patients with low and high levels of molecular markers of type II collagen synthesis and degradation at baseline.

Prediction of Joint Destruction by Baseline Levels of Serum PIIANP and Urinary CTX-II FIG. 2 shows two bar graphs representing analysis of progression of joint damage over one year in patients with low and high levels of molecular markers of type II collagen synthesis and degradation at baseline. Low levels of serum N-propeptide of type IIA procollagen (PIIANP) were those below the mean −1 SD of healthy controls. High levels of urinary C-terminal cross-linking telopeptide of type II collagen (CTX-II) were those which exceeded the mean +1 SD of healthy controls. The uncoupling Index was calculated as the Z-score of urinary CTX-II minus the Z-score of serum PIIANP. P values refer to the difference between the two groups of baseline levels of molecular markers.

Patients with knee OA were classified as low or high baseline serum PIIANP using as a cut-off the mean −1 SD of the controls and low or high baseline urinary CTX-II using as a cut-off the mean +1 SD of the controls. Using these cut-offs, 46% and 60% of patients were identified as having low serum PIIANP and high urinary CTX-II, respectively. As shown in FIG. 2, patients with low baseline serum PIIANP had a higher progression of joint destruction over one year, as assessed either by X-ray or arthroscopy, as compared to the other patients. Conversely, patients with high baseline levels of urinary CTX-II had a faster progression of joint destruction than patient with low levels of urinary CTX-II, although the difference between the two groups was significant only for the chondropathy score as assessed by arthroscopy (FIG. 2, right panel). Significantly, patients with both low baseline serum PIIANP and high urinary CTX-II, who accounted for 29% of the population, had an eight (8)-fold higher rate of progression of joint destruction over one year than the other patients ($p=0.012$ and $p<0.0001$, for X-ray and arthroscopy, respectively) (FIG. 2)

Patients with knee OA were characterized as progressors and non-progressors based on the changes over one year in JSW or VAS chondropathy score. There was no significant difference between progressors and non progressors for age, body mass index, disease duration, pain (VAS), Lesquesnes's functional index, proportion of patients with knee effusion, articular index, radiographic JSW and arthroscopy chondropathy VAS at baseline (data not shown). Patients who showed a significant progression of joint destruction assessed either by X-ray or arthroscopy had lower baseline values of serum PIIANP and increased urinary CTX-II than patients who did not progress, although the difference was significant only for urinary CTX-II (Table 2). The uncoupling index of type II collagen synthesis and degradation at baseline was again more sensitive than each marker alone to differentiate progressors and non-progressors with a 90 to 98% (p: 0.006-0.0024) higher baseline values of this index in patients who progressed during the study (Table 2).

Figure 3:
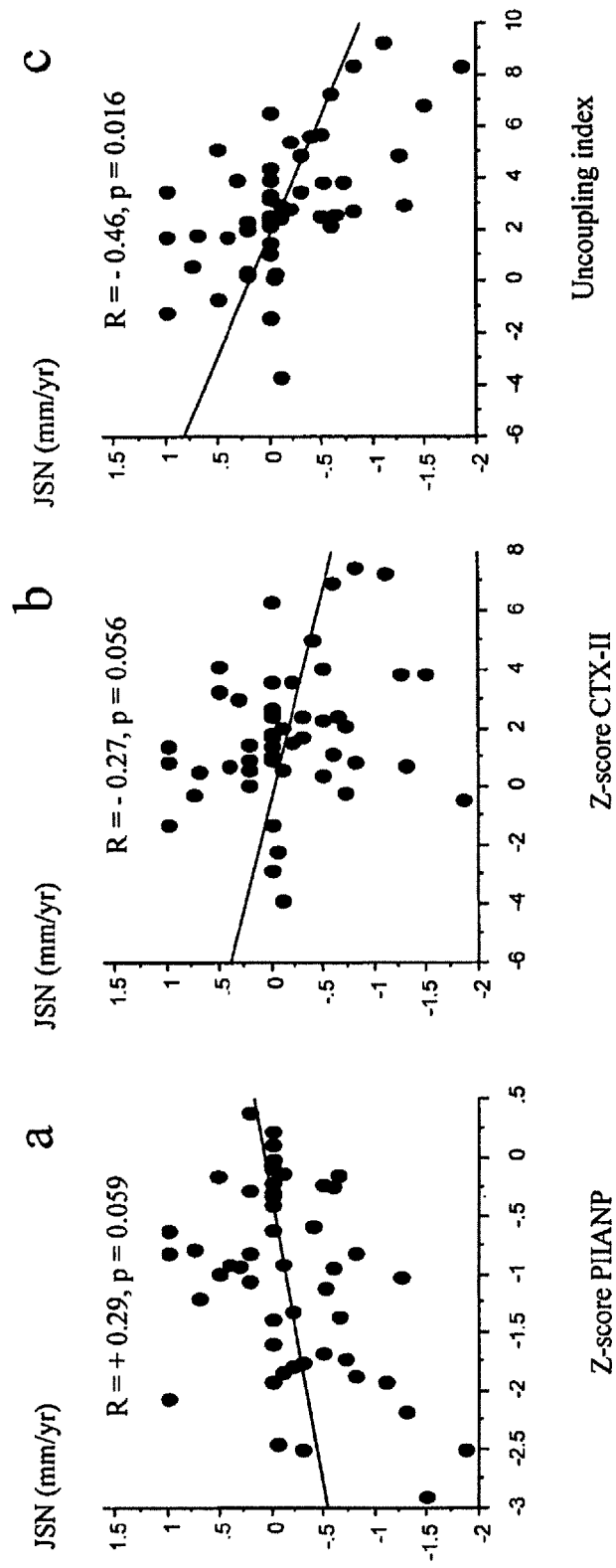
FIG. 3 shows graphical illustrations of the correlation between baseline levels of molecular markers of type II collagen synthesis and degradation and the one year change of knee joint space width in patients with knee OA.

FIG. 3 shows three scatter plots demonstrating the correlation between baseline levels of molecular markers of type II collagen synthesis and degradation, and the one year change of knee joint space width in patients with knee OA. Baseline levels of (a) serum N-propeptide of type IIA procollagen (PIIANP), and (b) urinary C-terminal cross-linking telopeptide of type II collagen (CTX-II), were expressed as a Z-score, i.e., in number of standard deviation from the mean values of healthy controls. The uncoupling index (c) was calculated as the Z-score of urinary CTX-II minus the Z-score of serum PIIANP. The regression lines, coefficients of correlation (R) and significance levels (p) were obtained from linear regression analyses.

When both baseline levels of molecular markers (Z-score) and changes in radiological JSW and VAS arthroscopic score of chondropathy over 12 months were considered as continuous variables, low levels of serum PIIANP and high levels of urinary CTX-II at baseline were associated with a higher progression of joint destruction (Table 3 and FIG. 3). The association was however only significant between urinary CTX-II and changes in VAS chondropathy score. The uncoupling index (Z-score CTX-II minus Z-score PIIANP) was a better predictor of joint destruction over one year than either serum PIIANP or urinary CTX-II alone, and highly significantly correlated with both changes in JSW ($p=0.0016$) and VAS score of chondropathy ($p=0.014$) (Table 3 and FIG. 3).

When baseline Z-scores of molecular markers were analyzed as continuous variables, increased serum PIIANP and urinary CTX-II were associated respectively with decreased and increased risk of progression, although the relative risk was significant only for CTX-II ($p=0.042$) when progression was assessed by arthroscopy (Table 4). Interestingly when the Z-scores of serum PIIANP and urinary CTX-II were combined in the uncoupling index, each unit increase of the index was significantly associated with increased risk of progression with relative risks of 1.7 ($p=0.008$) and 1.6 ($p=0.013$) for X-ray and arthroscopic progression, respectively (Table 4). It was then estimated that the risk of progression for levels of serum PIIANP and urinary CTX-II respectively below and above the upper limit of the reference range of healthy controls.

Figure 4:
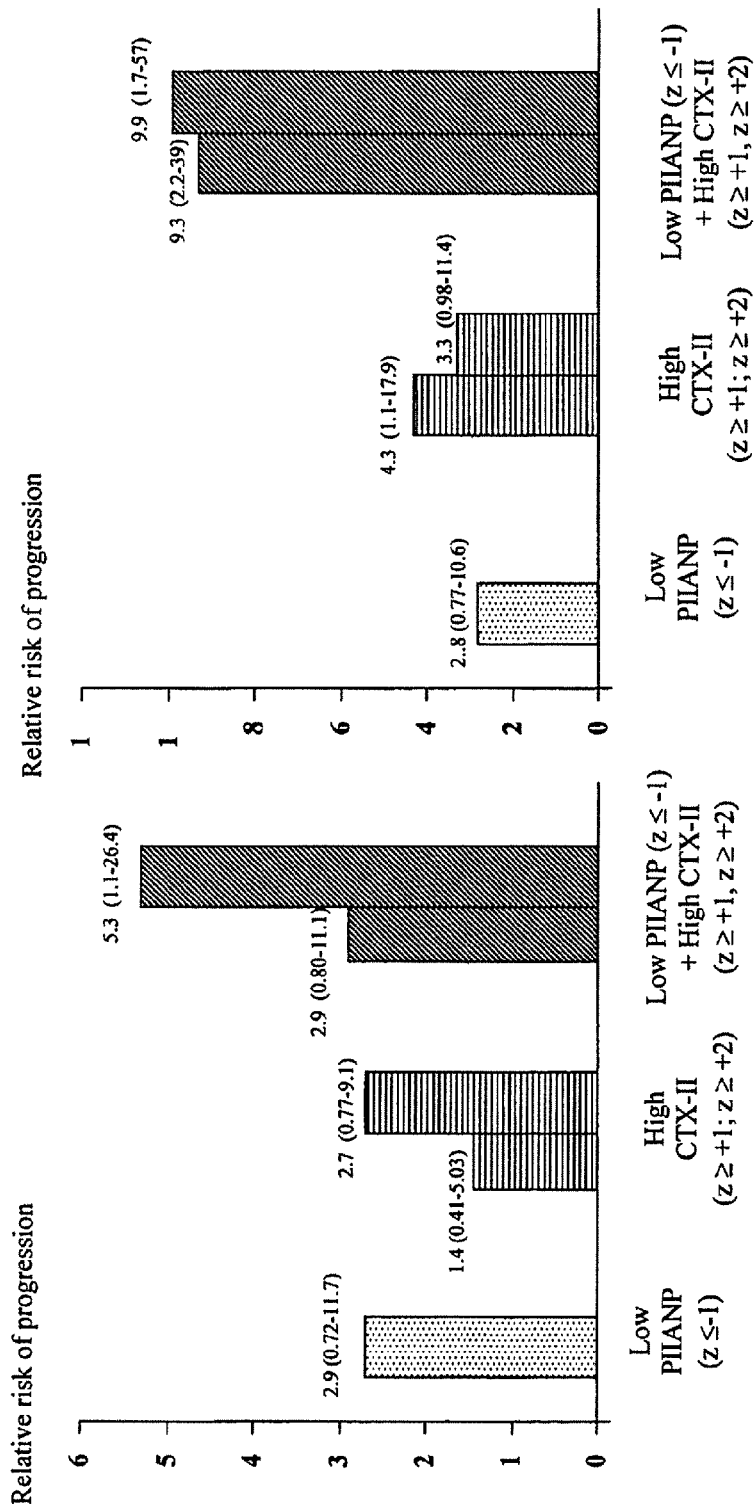
FIG. 4 shows graphical illustrations of the combination of measurements of molecular markers of type II synthesis and of degradation in an uncoupling index to identify patients with knee osteoarthritis at the highest risk of progression of joint damage.

FIG. 4 shows two bar graphs analyzing the combination of molecular markers of type II synthesis and degradation to identify patients with knee osteoarthritis at the highest risk of progression of joint damage. Low levels of serum N-propeptide of type IIA procollagen (PIIANP) were those below the mean −1 SD of healthy controls (Z-score −1). High levels of urinary C-terminal cross-linking telopeptide of type II collagen (CTX-II) were those which exceeded the mean +1 SD (Z-score +1) or the mean +2 SDs (Z-score+2) of healthy controls. Uncoupling Index was calculated as the Z-score of urinary CTX-II minus Z-score of serum PIIANP. The numbers over each bar indicate the relative risks (95% confidence intervals).

Patients with baseline levels of serum PIIANP ±mean−1 SD of healthy controls had a relative risk of progression of 2.9 and 2.8 (by X-ray and arthroscopy, respectively), although relative risks did not reach significance (FIG. 4). Patients with urinary CTX-II levels >mean +1 SD of controls had a relative risk of progression of 1.4 (0.4-5.0) and 4.3 (1.1-17.9) when progression was assessed by X-ray and arthroscopy, respectively. When high urinary CTX-II was defined as levels >mean +2 SDs, which identified a proportion of patients at risk similar to that of serum PIIANP (43%), the relative risk of progression were of 2.7 and 3.3, for X-ray and arthroscopy, respectively. Patients with both decreased serum PIIANP and increased urinary CTX-II had a higher risk of progression than patients with either low serum PIIANP or high urinary CTX-II (FIG. 4).

Figure 5:
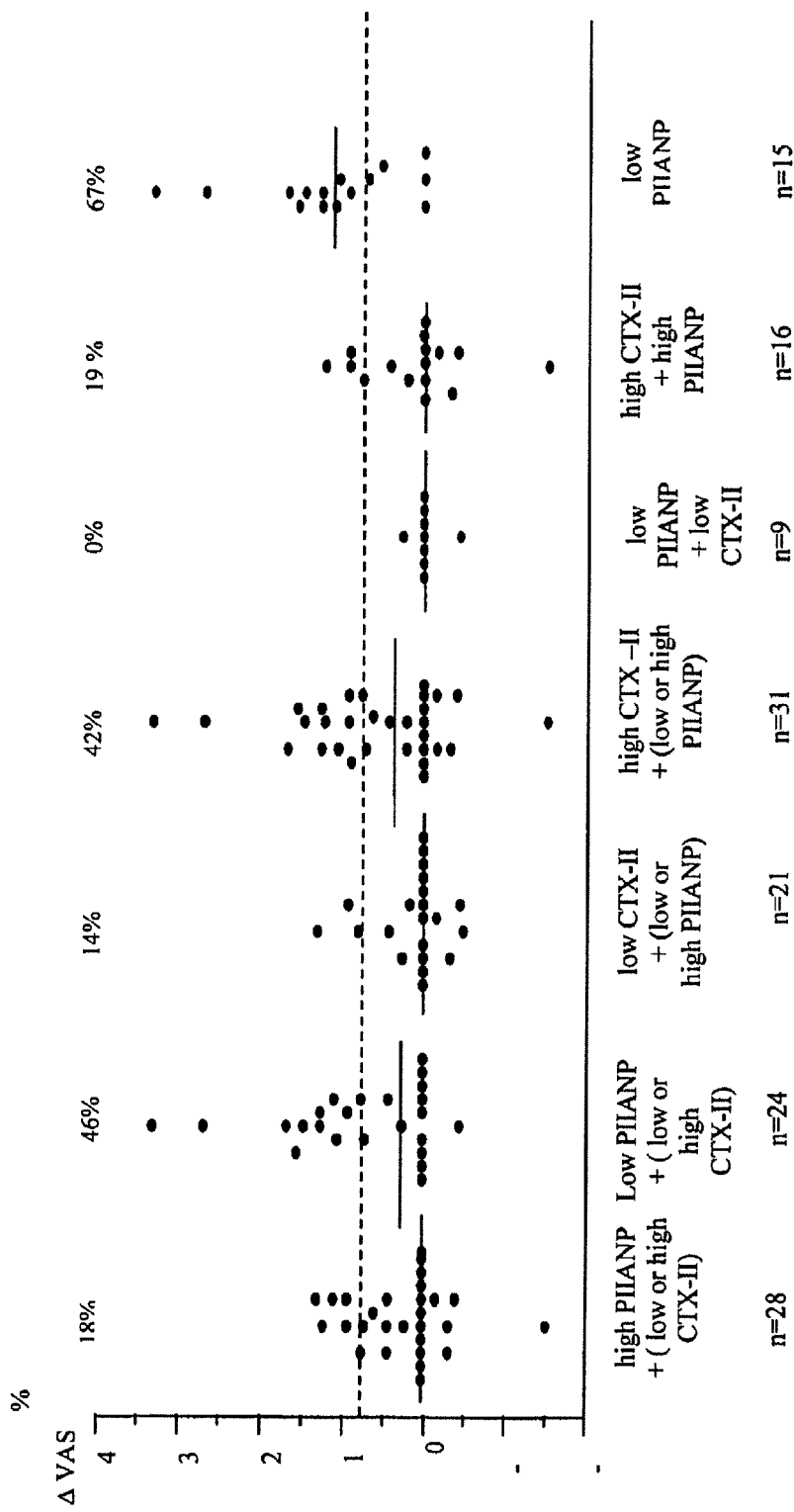
FIG. 5 is a graphical illustration of individual values of the one year changes in the visual analogue scale (VAS) score of chondropathy according to baseline levels of serum N-propeptide of type IIA procollagen (PIIANP) and urinary C-terminal cross-linking telopeptide of type II collagen (CTX-II).

FIG. 5 shows individual values of the one year changes in the visual analogue scale (VAS) score of chondropathy according to baseline levels of serum N-propeptide of type IIA procollagen (PIIANP) and urinary C-terminal cross-linking telopeptide of type II collagen (CTX-II). The cut-off used to separate patients with low and high levels of serum PIIANP was the mean −1 SD of healthy controls. The cut-off used to separate patients with high and low levels of CTX-II was the mean +1 SD of healthy controls. The plain horizontal lines represent the median of the one year change in VAS score in the different groups of patients. The horizontal dotted line represents the increase in VAS score over one year (8 units) used to define significant progression (see statistical analyses). The figures at the top represent the percentage of patients showing a significant progression of joint destruction that is with an increase of VAS score over one year >8 units.

Among patients with low PIIANP (irrespective of urinary CTX-II levels) or high CTX-II (irrespective of serum PIIANP levels), 46 and 42% of patients, respectively were identified as progressors. Among patients who had only one risk factor for progression, i.e., those having low PIIANP but low CTX-II or high CTX-II but high PIIANP, the proportion of progressors was small (0 and 19%, respectively). The proportion of progressors was highest (67%) among patients with both low PIIANP and high CTX-II.

In this example, using two newly developed molecular markers of type II collagen metabolism, patients with knee OA were characterized for an uncoupling of type II collagen synthesis and degradation. More importantly, it was discovered that the combination of markers of synthesis and catabolism of type II collagen in an uncoupling index is highly predictive of the progression of joint damage showing that this index is useful to identify patients at high risk for cartilage degradation, including osteoarthritis and rheumatoid arthritis patients.

This results set forth in this example confirm that serum PIIANP is decreased compared to controls (Rousseau, supra) suggesting a deficit of type II collagen synthesis and thus of cartilage repair. It was also confirmed that the rate of cartilage breakdown, and more specifically of type II collagen degradation, is increased in OA in agreement with two recent previous smaller studies using this marker and with histological experiments showing increased type II collagen damage in OA cartilage. No correlation was found between serum PIIANP and urinary CTX-II in patients with knee OA suggesting that the rate of synthesis of type II collagen molecules is independent of the rate of degradation of resident molecules within cartilage matrix in favor of an uncoupling of these two activities. Accordingly, the combination of a marker of cartilage synthesis (serum PIIANP) with that of catabolism (urinary CTX-II) in an uncoupling index allows accurate and precise discrimination between patients with knee OA and controls as compared with using one of these two markers alone.

One of the main uses of the molecular markers of the invention is to identify patients at high risk for rapid progression of joint destruction who would benefit from chondroprotective therapy, rather than for the diagnosis of OA. Indeed, clinical indices such as pain and physical function score are poorly related to the destruction of joint structure as was confirmed in this study that there was no association between pain, Lesquesne's functional index, knee effusion and progression. At baseline, a weak and non significant association between increased urinary CTX-II levels and a lower joint space width in agreement with a previous cross-sectional study in patients with knee OA (Garnero, Ann. Rheum. Dis. 60, supra) was found, whereas serum PIIANP was not predictive. These data suggest that levels of molecular markers alone are poorly predictive of the current extent of joint damage.

Longitudinal studies investigating the values of molecular markers to predict progression of joint damage are scarce. A predictive value of serum C-reactive protein (Spector, T. D., et al., Low-levels increases in serum C-reactive protein are present in early osteoarthritis of the knee and predict progressive disease, Arthritis Rheum. 40:723-727 (1997)), COMP (Sharif, M., et al., Relationship between serum cartilage oligomeric matrix protein levels and disease progression in osteoarthritis of the knee joint, Brit. J. Rheumatol. 34:306-310 (1995); Conrozier, T., et al., Serum concentrations of cartilage oligomeric matrix protein and bone sialoprotein in hip osteoarthritis: A one year prospective study, Ann. Rheum. Dis. 9:527-532 (1998)) and hyaluronic acid (Sharif, M., et al., Serum hyaluronic acid level as a predictor of disease progression in osteoarthritis of the knee, Arthritis Rheum. 38:760-767 (1995)) has been found in some but not all studies (Georges, C., et al., Serum biologic markers as predictors of disease progression in osteoarthritis of the knee, Arthritis Rheum. 40:590-591 (1997)). However, molecular markers investigated in these previous studies were not specific of joint tissue (Garnero, Arthritis Rheum. 43, supra) and none of them evaluated the metabolism of type II collagen, the main abundant protein of cartilage matrix.

In a longitudinal evaluation, lower baseline levels of serum PIIANP and higher urinary levels of CTX-II were found to be associated with increased rate of progression of joint damage over one year evaluated either by X-rays or arthroscopy, in agreement with the concept that a decreased reparative process and increased degradation of cartilage matrix will lead to an accelerated rate of joint degradation. When used separately, the association between baseline levels of these two markers and progression was however modest and non consistent across all analyses. In contrast, when serum PIIANP and urinary CTX-II were combined in an uncoupling index of type II collagen synthesis and degradation, a highly significant correlation was found with progression of joint destruction assessed either by X-ray or arthroscopy. This index accounted for up to 21% of the inter-individual variability of the progression rate and each unit increase of this index was associated with 60 to 70% increase in the risk of progression. In addition, patients with both low levels of serum PIIANP and high urinary CTX-II who accounted for about 29% of the population had a 3 to 9 fold increased risk of progression suggesting that this new index may indeed be an important new risk factor for progression of joint damage.

The benefits of the present invention include, in an exemplary embodiment, providing a method for detecting or predicting cartilage destruction in a subject, the method comprising detecting an uncoupling of type II collagen synthesis from type II collagen degradation in the subject. Detecting the uncoupling of type II collagen synthesis from type II collagen degradation in the subject comprises, for example, (a) detecting both a synthesis marker and degradation marker in a biological sample of the subject, (b) comparing the amounts of the synthesis marker and degradation marker, and (c) correlating the relative amounts of the synthesis marker and degradation marker with predetermined standards to detect cartilage destruction in the subject. In one embodiment, step (b) is performed at least twice. In another embodiment, step (a) is a single step.

Preferably, the synthesis marker is PIIANP and the degradation marker is selected from the group consisting of CTX-II, Type II collagen, Type VI collagen, COMP, keratin sulfate, link protein, aggrecan, and aggrecan fragments. The detection step (a) may also be performed by an assay selected from the group consisting of radioimmunoassays, enzyme immunoassays, ligand assays, immunoradiometric assays, fluoroimmunoassays, and enzyme-linked immunosorbent assays. When the assay is an enzyme-linked immunosorbent assay, it is preferably one of a competitive ELISA or sandwich ELISA.

The biological samples are preferably selected from the group consisting of blood, serum, urine, sputum, interstitial fluid, joint debris, cartilage fragments and synovial cells. Preferably, the biological sample is cartilage, more preferably knee cartilage. Another embodiment includes performing the above method on a subject which is a mammal. Preferably, the mammal is a human. In another aspect of the invention, the subject is receiving therapeutic treatment for said cartilage degeneration condition while the above method is being performed. The cartilage degeneration condition may be rheumatoid arthritis and osteoarthritis, but may include other cartilage degeneration conditions having synthesis and degradation markers which may be examined by uncoupling analysis.

In another embodiment, there is provided a method for determining the progress of osteoarthritis or cartilage destruction in a subject comprising quantifying the uncoupling of type II collagen synthesis from type II collagen degradation in the subject. The quantification comprises, for example, (a) measuring an amount of a synthesis marker in a biological sample of the subject, (b) measuring an amount of a degradation marker in the biological sample of the subject, (c) calculating a value of an uncoupling index using the amount of synthesis marker and the amount of degradation marker, and (d) comparing the value of the uncoupling index with predetermined standards to quantify the status of osteoarthritis or cartilage destruction in the subject. Steps (a) and (b) can be performed by an assay selected from the group consisting of radioimmunoassays, enzyme immunoassays, ligand assays, immunoradiometric assays, fluoroimmunoassays, and enzyme-linked immunosorbent assays. Suitable enzyme-linked immunosorbent assays include competitive ELISAs and sandwich ELISAs. The sample is, for example, blood, serum, urine, sputum, interstitial fluid, joint debris, cartilage fragments and synovial cells. In an exemplary embodiment, the osteoarthritis cartilage synthesis marker is PIIANP, and the method the osteoarthritis cartilage degradation marker is selected from the group consisting of CTX-II, Type II collagen, Type VI collagen, COMP, keratin sulfate, link protein, aggrecan, and aggrecan fragments.

In another embodiment, a method is provided for detecting or predicting cartilage degeneration in a subject, the method comprising the steps of (a) providing a first and a second body fluid sample, wherein the first sample is taken from a subject from which status of cartilage degeneration is to be determined and the second sample is taken from the same subject at a later time; (b) providing a first antibody, second antibody, third labeled antibody, and fourth labeled antibody, wherein the first antibody is capable of specifically binding to a human collagen synthesis marker, the second antibody is capable of specifically binding to a human collagen degradation marker, the third labeled antibody is capable of binding to the human collagen synthesis marker, and the fourth labeled antibody is capable of binding to the human collagen degradation marker, and a detecting reagent capable of detecting the label; (c) contacting the first antibody, second antibody, third labeled antibody, fourth labeled antibody, and the detecting reagent with the first body fluid sample; (d) contacting the first antibody, second antibody, third labeled antibody, fourth labeled antibody, and the detecting reagent with the second body fluid sample; and, (e) detecting the amount of and determining the concentration of human collagen synthesis marker and collagen degradation marker in the first sample to provide a reference value and detecting the amount of and determining the concentration of human collagen synthesis marker and collagen degradation marker in the second sample, wherein an increased concentration of human collagen degradation marker coupled with a decreased concentration of collagen synthesis marker in the second sample compared to the reference value indicates that the test subject has a high probability of having had or being at risk of progressive cartilage degeneration.

The concentration of human collagen degradation marker and synthesis marker in both the first and second body fluid samples from the subject may be determined by an immunological assay. Preferably, the immunological assay is selected from the group consisting of radioimmunoassays, enzyme immunoassays, ligand assays, immunoradiometric assays, fluoroimmunoassays, and enzyme-linked immunosorbent assays. More preferably, an enzyme-linked immunosorbent assay is used which is either a competitive ELISA or sandwich ELISA. The body fluid sample of step (a) is preferably selected from the group consisting of blood, serum, urine, sputum, interstitial fluid, joint debris, cartilage fragments and synovial cells.

In another embodiment, to indicate that the test subject has a high probability of having or being at risk of having progressive cartilage degeneration, the amount of collagen degradation marker in the second sample is greater than a reference value defined as a mean value plus one standard deviation of the collagen degradation marker concentration in the first sample. In a second aspect of this embodiment, to indicate that the test subject has a high probability of having or being at risk of having progressive cartilage degeneration, the amount of collagen synthesis marker in the second sample is less than a reference value defined as a mean value plus one standard deviation of the collagen synthesis marker concentration in the first sample. Preferably, both indications are combined to indicate whether a test subject has a high probability of having or being at risk of having progressive cartilage degeneration whereby (a) to indicate that the test subject has a high probability of having or being at risk of having progressive cartilage degeneration, the amount of collagen degradation marker in the second sample is greater than a reference value defined as a mean value plus one standard deviation of the collagen degradation marker concentration in the first sample; and (b) to indicate that the test subject has a high probability of having or being at risk of having progressive cartilage degeneration, the amount of collagen synthesis marker in the second sample is less than a reference value defined as a mean value plus one standard deviation of the collagen synthesis marker concentration in the first sample.

The first antibody and second antibody of the above method may be immobilized on a solid surface. Preferably, the solid surface is a microtiter plate or a dip stick. In another embodiment of the above method, the solid surface is an instrument in contact with a human joint or a human bloodstream. In an exemplary embodiment of the solid support, the osteoarthritis cartilage synthesis marker is PIIANP, and the osteoarthritis cartilage degradation marker is selected from the group consisting of CTX-II, Type II collagen, Type VI collagen, COMP, keratin sulfate, link protein, aggrecan, and aggrecan fragments.

In the methods, contacting the first antibody, second antibody, third labeled antibody, fourth labeled antibody, and the detecting reagent with the first body fluid sample may be performed simultaneously. Alternatively, contacting the first antibody, second antibody, third labeled antibody, fourth labeled antibody, and the detecting reagent with the first body fluid sample may be performed sequentially. In another aspect, contacting the first antibody, second antibody, third labeled antibody, fourth labeled antibody, and the detecting reagent with the second body fluid sample may be performed simultaneously. Alternatively, contacting the first antibody, second antibody, third labeled antibody, fourth labeled antibody, and the detecting reagent with the second body fluid sample may be performed sequentially.

In another embodiment of the method, the label of the third and fourth labeled antibodies may comprise biotin, and the third and fourth antibodies may be detected by the method further providing a composition conjugated to streptavidin and adding the composition to the contacted first antibody or second antibody, third labeled antibody, and fourth labeled antibody, wherein the composition is directly detectable or the composition generates a second directly detectable composition. Preferably, the detectable composition is an enzyme, the enzyme preferably being a peroxidase, more preferably horseradish peroxidase. In another aspect, the above enzyme generates a detectable colored composition.

In another embodiment of the above method, the first antibody or the second antibody is a monoclonal antibody or a polyclonal antibody. Preferably, the first antibody is a monoclonal antibody and the second antibody is a polyclonal antibody. In another aspect, the cartilage synthesis marker is PIIANP and the cartilage degradation marker is selected from the group consisting of CTX-II, Type II collagen, Type VI collagen, COMP, keratin sulfate, link protein, aggrecan, and aggrecan fragments. In addition, the above method steps (a) through (e) may be automated.

The patient of the above method may be receiving therapeutic treatment for said cartilage degeneration condition at the same time the method is being performed. The status to be detected by the above method may be progression, decrease or stability of said cartilage degeneration condition. The cartilage degeneration condition may be rheumatoid arthritis, osteoarthritis or other cartilage degeneration conditions detectable by uncoupling synthesis and degradation biological markers.

In yet another embodiment, the method for detecting or predicting cartilage degeneration in a subject may comprise the steps of (a) providing a body fluid sample, wherein the sample is taken from a subject from which status of cartilage degeneration is to be determined; (b) providing a first antibody, second antibody and a third labeled antibody, wherein the first antibody is capable of specifically binding to a human collagen synthesis marker, the second antibody is capable of specifically binding to a human collagen degradation marker, and the third labeled antibody is capable of binding to both the human collagen synthesis marker and human collagen degradation marker, and a detecting reagent capable of detecting the label; (c) contacting the first antibody, second antibody, and the third labeled antibody, and the detecting reagent with the body fluid sample; (d) contacting the first antibody, second antibody and the third labeled antibody, and the detecting reagent with the body fluid sample; and, (e) detecting the amount of and determining the concentration of human collagen synthesis marker and collagen degradation marker in the sample, wherein a concentration of human collagen degradation marker greater than one standard deviation above a predetermined reference value uncoupled with a decreased concentration of collagen synthesis marker less than one standard deviation below a predetermined reference value indicates that the test subject has a high probability of having had or being at risk of progressive cartilage degeneration.

The cartilage degeneration condition of the above method may be rheumatoid arthritis, osteoarthritis or other cartilage degeneration conditions detectable by uncoupling biological markers associated with the condition.

In another embodiment, there is provided a solid support in contact with a combination of a first antibody and second antibody, wherein the first antibody is capable of specifically binding to a human collagen synthesis marker and the second antibody is capable of specifically binding to a human collagen degradation marker. The first antibody and second antibody of the above method may be immobilized on a solid surface such as a microtiter plate or a dip stick. In another embodiment, the solid surface is an instrument in contact with a human joint or a human bloodstream. The osteoarthritis cartilage synthesis marker is, for example, PIIANP, and the osteoarthritis cartilage degradation marker is, for example, selected from the group consisting of CTX-II, Type II collagen, Type VI collagen, COMP, keratin sulfate, link protein, aggrecan, and aggrecan fragments.

In another embodiment, there is provided a kit for detecting the progression of osteoarthritis comprising instructions setting forth a method comprising the following: (a) providing a first and a second body fluid sample, wherein the first sample is taken from a subject from which status of osteoarthritis is to be determined and the second sample is taken from the same subject at a later time, and (b) detecting the amount of and determining the concentration of human collagen synthesis marker and collagen degradation marker in the first sample to provide a reference value, and detecting the amount of and determining the concentration of human collagen synthesis marker and collagen degradation marker in the second sample, wherein an increased concentration of human collagen degradation marker coupled with a decreased concentration of collagen synthesis marker in the second sample compared to the reference value indicates that the test subject has a high probability of having had or being at risk of progressive osteoarthritis.

In one embodiment of the kit, the kit includes a first antibody, second antibody and a third labeled antibody, wherein the first antibody is capable of specifically binding to a human collagen synthesis marker, the second antibody is capable of specifically binding to a human collagen degradation marker, and the third labeled antibody is capable of binding to both the human collagen synthesis marker and human collagen degradation marker, and a detecting reagent capable of detecting the label. The instructions setting forth the method further include the following, (a) providing a first antibody, second antibody and a third labeled antibody, wherein the first antibody is capable of specifically binding to a human collagen synthesis marker, the second antibody is capable of specifically binding to a human collagen degradation marker, and the third antibody is capable of binding to both the human collagen synthesis marker and human collagen degradation marker, and a detecting reagent capable of detecting the label, (b) contacting the first antibody, second antibody, and the third labeled antibody, and the detecting reagent with the first body fluid sample, and (c) contacting the first antibody, second antibody and the third labeled antibody, and the detecting reagent with the second body fluid sample to detect the amount of and determine the concentration of human collagen synthesis marker and collagen degradation marker in the first sample to provide a reference value, and to detect the amount of and determine the concentration of human collagen synthesis marker and collagen degradation marker in the second sample.

In another embodiment of the kit, the kit includes a first antibody, second antibody third labeled antibody, and fourth labeled antibody, wherein the first antibody is capable of specifically binding to a human collagen synthesis marker, the second antibody is capable of specifically binding to a human collagen degradation marker, the third labeled antibody is capable of binding to a human collagen synthesis marker and the fourth labeled antibody is capable of binding to a human collagen degradation marker, and a detecting reagent capable of detecting the label. The instructions for detecting the amount of and determining the concentration of human collagen synthesis marker and collagen degradation marker in the first sample to provide a reference value, and for detecting the amount of and determining the concentration of human collagen synthesis marker and collagen degradation marker in the second sample, include the following steps: (a) providing a first and a second body fluid sample, wherein the first sample is taken from a subject from which status of cartilage degeneration is to be determined and the second sample is taken from the same subject at a later time; (b) providing a first antibody, second antibody, third labeled antibody, and fourth labeled antibody, wherein the first antibody is capable of specifically binding to a human collagen synthesis marker, the second antibody is capable of specifically binding to a human collagen degradation marker, the third labeled antibody is capable of binding to the human collagen synthesis marker, and the fourth labeled antibody is capable of binding to the human collagen degradation marker, and a detecting reagent capable of detecting the label; (c) contacting the first antibody, second antibody, third labeled antibody, fourth labeled antibody, and the detecting reagent with the first body fluid sample; (d) contacting the first antibody, second antibody, third labeled antibody, fourth labeled antibody, and the detecting reagent with the second body fluid sample; and, (e) detecting the amount of and determining the concentration of human collagen synthesis marker and collagen degradation marker in the first sample to provide a reference value and detecting the amount of and determining the concentration of human collagen synthesis marker and collagen degradation marker in the second sample, wherein an increased concentration of human collagen degradation marker coupled with a decreased concentration of collagen synthesis marker in the second sample compared to the reference value indicates that the test subject has a high probability of having had or being at risk of progressive cartilage degeneration.

Thus, the invention generally relates to methods, kits and articles of manufacture for detecting and determining the progression of cartilage degeneration diseases, such as osteoarthritis and rheumatoid arthritis, by quantitating collagen synthesis and degradation markers in patient samples. Using the invention, one can determine whether a cartilage degeneration condition is progressing, regressing, or remaining stable by quantitating collagen synthesis and degradation markers in patient samples and comparing the value obtained to a reference value. When a joint affected by cartilage degeneration in question expresses collagen synthesis and degradation markers, a change in this value is indicative of a change in the progression of the cartilage degeneration condition. The methods and apparatus of the invention allow accurate determination of the therapeutic effects certain cartilage degeneration drug treatments, including osteoarthritis and rheumatoid arthritis drug treatments, so are also useful for pharmaceutical efficacy studies in mammals.

TABLE 1

Baseline characteristics of patients with knee osteoarthritis and healthy controls

|  | Knee OA (n = 75) | Controls (n = 58) | P value |
|---|---|---|---|
| Demographic |  |  |  |
| Gender(F/M) | 51/24 | 38/20 | 0.91 |
| Age (years) | 63 ± 8 | 63 ± 8 | 0.98 |
| Weight (kg) | 78.6 ± 14 | 68.4 ± 14.3 | <0.001 |
| Height (cm) | 163 ± 8 | 161 ± 9.0 | 0.38 |
| Body Mass Index | 29.5 ± 4.5 | 26.2 ± 3.7 | <0.001 |
| Clinical activity |  |  |  |
| Disease duration (month) | 58 ± 62 | — |  |
| Pain (100-mmVAS) | 51.8 ± 17.5 | — |  |
| Lequesne's functional index | 8.8 ± 2.96 | — |  |
| Knee effusion (yes/no) | 28/46 | — |  |
| Articular score | 283 ± 125 | — |  |
| Assessment of femorotibial compartment |  |  |  |
| Joint space width (X-ray, mm) | 3.98 ± 1.46 | — |  |
| Arthroscopic evaluation of chondropathy (100-mmVAS) | 40.1 ± 19.4 | — |  |

Results are shown as mean ± SD

TABLE 2

Baseline levels of molecular markers of type II collagen metabolism of 52 patients with knee OA with or without progression of joint damage

| | one year progression in | | | | | |
|---|---|---|---|---|---|---|
| | Joint space narrowing (X-ray) | | | 100 mm-VAS chondropathy (Arthroscopy) | | |
| Molecular Markers at baseline | Yes* (n = 16) | No (n = 36) | p | Yes* (n = 16) | No (n = 36) | p |
| Serum PIIANP† (ng/ml) | 17.8 ± 5.7 | 20.1 ± 5.4 | 0.20 | 18.2 ± 6.1 | 20.2 ± 5.2 | 0.25 |
| Urinary CTX-II† (ng/mmol Cr) | 819 ± 566 | 539 ± 259 | 0.04 | 764 ± 429 | 549 ± 361 | 0.032 |
| Uncoupling Index‡ | 4.84 ± 2.50 | 2.45 ± 2.07 | 0.0024 | 4.49 ± 2.57 | 2.36 ± 2.26 | 0.006 |

*progressors were patients with a decreases in joint space width of 0.5 mm or more or an increase in VAS chondropathy score > + 8 units at one year.
†PIIANP: N-propeptide of type IIA procollagen; CTX-II: C-terminal cross-linking telopeptide of type II collagen
‡Calculated as the Z-score of urinary CTX-II minus Z-score of PIIANP.
Results are shown as mean ± SD

TABLE 3

Association between baseline levels of molecular markers of type II collagen metabolism and one year changes in X-ray and arthroscopic evaluation of the femorotibial compartment of 52 patients with knee osteoarthritis

| | one year change in | | | |
|---|---|---|---|---|
| | Joint Space Width (X-Ray) | | 100-mm VAS chondropathy (Arthroscopy) | |
| Molecular Markers at baseline (Z-score) | r* | p* | r* | p* |
| Serum PIIANP† | 0.29 | 0.059 | −0.26 | 0.088 |
| Urinary CTX-II† | −0.27 | 0.056 | 0.29 | 0.037 |
| Uncoupling index‡ | −0.46 | 0.0016 | 0.36 | 0.014 |

*r and p values were obtained from linear regression analyses between the Z-score of each marker at baseline and the one year changes of joint space width and VAS chondropathy score.
†PIIANP: N-propeptide of type IIA procollagen; CTX-II: C-terminal cross-linking telopeptide of type II collagen.
‡Calculated as the Z-score of urinary CTX-II minus Z-score of serum PIIANP.

TABLE 4

Association between baseline levels of molecular markers of type II collagen metabolism and the risk of progression of joint damage over one year

| | Relative risk of progression* (95% CI) for 1 SD increase in the markers | |
|---|---|---|
| Molecular markers at baseline (Z-score) | Joint space narrowing (X-ray) | 100 mm-VAS chondropathy score (arthroscopy) |
| Serum PIIANP† | 0.57 (0.24-1.3) | 0.61 (0.27-1.39) |
| Urinary CTX-II† | 1.33 (0.99-1.78) | 1.35 (1.01-1.81) |
| Uncoupling index‡ | 1.70 (1.15-2.49) | 1.60 (1.10-2.19) |

*progression was defined by a decrease of joint space width of 0.5 mm or more or an increase in VAS chondropathy score > + 8 units at one year.
†PIIANP: N-propeptide of type IIA procollagen;
CTX-II: C-terminal cross-linking telopeptide of type II collagen
‡Calculated as the Z-score of urinary CTX-II minus Z-score of PIIANP.

Other Embodiments

The invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

References Cited

All references cited above are incorporated herein by reference in their entirety and for all purposes to the same extent as if each individual publication, patent or patent application was specifically and individually indicated to be incorporated by reference in its entirety for all purposes. Citation of a reference herein shall not be construed as an admission that such is prior art to the present invention.

What is claimed is:

1. A method for detecting cartilage destruction in a subject, said method comprising calculating an uncoupling index for the uncoupling of type II collagen synthesis from type II collagen degradation in one or more biological samples from the subject, wherein detecting an uncoupling of type II collagen synthesis from type II collagen degradation in the subject comprises:
   (a) quantitating both a marker of cartilage synthesis and a marker of cartilage degradation in the one or more biological samples of the subject, the samples being of the same source obtained within a 24 hour period;
   (b) comparing the amounts of the marker of cartilage synthesis and the marker of cartilage degradation with, respectively, the amounts of the marker of cartilage synthesis and the marker of cartilage degradation in a healthy individual;
   wherein an uncoupling index score indicating an amount of cartilage degradation marker greater than 1 standard deviation above that found in a healthy individual, and an amount of cartilage synthesis marker greater than 1 standard deviation below that found in a healthy individual, indicates cartilage destruction in the subject.

2. The method of claim 1, wherein step (b) is performed at least twice.

3. The method of claim 1, wherein step (a) is a single step.

4. The method of claim 1, wherein the cartilage synthesis marker is the N-propeptide of type IIA procollagen (PIIANP).

5. The method of claim 1, wherein the cartilage degradation marker is selected from the group consisting of C-terminal cross-linking telopeptide of type II collagen (CTX-II), Type II collagen, Type VI collagen, cartilage oligomeric matrix protein (COMP), keratin sulfate, link protein, aggrecan, and aggrecan fragments.

6. The method of claim 1, wherein the detection of step (a) is performed by an assay selected from the group consisting of radioimmunoassays, enzyme immunoassays, ligand assays, immunoradiometric assays, fluoroimmunoassays, and enzyme-linked immunosorbent assays.

7. The method of claim 6, wherein the enzyme-linked immunosorbent assay is selected from the group consisting of competitive ELISAs and sandwich ELISAs.

8. The method of claim 1, wherein the biological sample is selected from the group consisting of blood, serum, urine, joint debris, cartilage fragments and synovial cells.

9. The method of claim 1, wherein the subject is a mammal.

10. The method of claim 9, wherein the mammal is a human.

11. The method of claim 1, wherein the biological sample is cartilage.

12. The method of claim 11, wherein the cartilage is knee cartilage.

13. A method of detecting cartilage destruction in a subject, comprising detecting uncoupling of type II cartilage synthesis from type II cartilage degradation in a subject;
   wherein the detecting uncoupling comprises simultaneously measuring
      the amount of the N-propeptide of type IIA collagen (PIIANP) from the serum of the subject, and
      the amount of the C-terminal cross-linking telopeptide of type II collagen (CTX-II) in the urine of the subject; and
   statistically comparing the values obtained by the measuring of PIIANP and CTX-II against healthy individuals not exhibiting cartilage destruction or osteoarthritis; wherein
   detection of the serum PIIANP levels of the subject less than one standard deviation below the values of PIIANP measured in a healthy individual; and
   detection of the urinary CTX-ll levels of the subject greater than one standard deviation above the values of CTX-ll measured in a healthy individual provides detection of cartilage degradation in the subject.

* * * * *